US012622958B2

(12) United States Patent
Quan et al.

(10) Patent No.: US 12,622,958 B2
(45) Date of Patent: May 12, 2026

(54) VIRUS-LIKE PARTICLES CONTAINING RSV ANTIGEN PROTEIN AND VACCINES USING THE SAME

(71) Applicant: University-Industry Cooperation Group of Kyung Hee University, Yongin-si (KR)

(72) Inventors: Fu-Shi Quan, Seoul (KR); Ki-Back Chu, Seoul (KR); Su-Hwa Lee, Seoul (KR)

(73) Assignee: University-Industry Cooperation Group of Kyung Hee University, Yongin-si (KR)

( * ) Notice: Subject to any disclaimer, the term of this patent is extended or adjusted under 35 U.S.C. 154(b) by 792 days.

(21) Appl. No.: 18/052,402

(22) Filed: Nov. 3, 2022

(65) Prior Publication Data

US 2023/0201330 A1     Jun. 29, 2023

(30) Foreign Application Priority Data

Dec. 14, 2021    (KR) ........................ 10-2021-0178199

(51) Int. Cl.
| | |
|---|---|
| *A61K 39/155* | (2006.01) |
| *A61K 39/39* | (2006.01) |
| *A61P 31/14* | (2006.01) |
| *C12N 7/00* | (2006.01) |

(52) U.S. Cl.
CPC ............ *A61K 39/155* (2013.01); *A61K 39/39* (2013.01); *A61P 31/14* (2018.01); *C12N 7/00* (2013.01)

(58) Field of Classification Search
None
See application file for complete search history.

(56) References Cited

U.S. PATENT DOCUMENTS

| | | | | |
|---|---|---|---|---|
| 8,715,692 B2 * | 5/2014 | Pushko | ................... | A61P 37/04 |
| | | | | 435/325 |
| 2013/0122032 A1 | 5/2013 | Smith et al. | | |

| | | | |
|---|---|---|---|
| 2015/0306207 A1 | 10/2015 | Smith et al. | |
| 2015/0333573 A1 | 11/2015 | Smith et al. | |
| 2017/0319682 A1 | 11/2017 | Smith et al. | |

FOREIGN PATENT DOCUMENTS

| | | |
|---|---|---|
| JP | 2020-089384 A | 6/2020 |
| KR | 20140077169 | 6/2014 |
| KR | 10-1862137 B1 | 5/2018 |
| WO | 2019/191623 A1 | 10/2019 |
| WO | 2020/092365 A1 | 5/2020 |

OTHER PUBLICATIONS

Zhang et al., Viruses, 2024, 16, 1701, 19 pages (Year: 2024).*
Tartof et al., JAMA Network Open, 2024, 7(12):e2450832, 10 pages (Year: 2024).*
Principi et al., Vaccines, 2025, 13, 717, 12 pages (Year: 2025).*
Office Action for Korean patent application No. 10-2021-0178199, dated May 21, 2024, 11 pages.
Li, Junwu et al., (Full Length Research Paper) "Construction of a fusion gene containing hepatitis B virus L gene and *Mycobacterium tuberculosis* Ag85B gene and its expression in Pichia pastoris"; Department of Microbiology and Immunology, Medical College, Jinan University, Guangzhou, China (Accepted Aug. 11, 2011); African Journal of Biotechnology vol. 10(60), pp. 12840-12846, Oct. 5, 2011; Available online at http://www.academicjournals.org/AJB; DOI: 10.5897/AJB11.190.
Lee, S. H. et al. "Virus-like particle vaccines expressing Toxoplasma gondii rhoptry protein 18 and microneme protein 8 provide enhanced protection" Vaccine (2018) vol. 36, Issue 38, 5692-5700.
Notice of Allowance issued in corresponding KR patent application Serial No. 10-2021-0178199, dated Mar. 12, 2025, with machine English translation.

* cited by examiner

*Primary Examiner* — Stacy B Chen
(74) *Attorney, Agent, or Firm* — Westman, Champlin & Koehler, P.A.; Amanda M. Prose

(57) ABSTRACT

An RSV virus-like particle which includes a chimeric protein that includes a core consisting of an influenza M1 protein, an RSV-derived preF protein, an RSV-derived G protein or part of G protein displayed on the surface of the core, can exhibit excellent effects in terms of inhibiting RSV virus infection and inhibiting the inflammatory response of the lungs.

6 Claims, 18 Drawing Sheets

Specification includes a Sequence Listing.

FIG. 1
| 1st tandem | | 2nd tandem | |
|---|---|---|---|
| Glycoprotein (1-261 pb) | | Glycoprotein (150-260 pb) | TM-CT |
|---|---|---|---|
4x Gly linker
FIG. 2
Pre-F VLPs
200 nm
Pre-F+G VLPs
200 nm
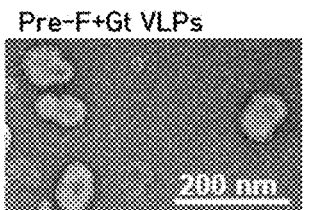
Pre-F+Gt VLPs
200 nm
FIG. 3
Fusion band
| kDa | 30 | 6 | |
|---|---|---|---|
| 63 | | | pre-F |
| 63 | | | pre-F+G |
| 63 | | | pre-F+Gt |
Glycoprotein band
| kDa | 30 | 6 | |
|---|---|---|---|
| 70 | | | G |
| 70 | | | Gt |
| 70 | | | pre-F+G |
| 70 | | | pre-F+Gt |
M1 band
| kDa | 30 | 6 | |
|---|---|---|---|
| 25 | | | pre-F |
| 25 | | | pre-F+G |
| 25 | | | pre-F+Gt |
| 25 | | | G |
| 25 | | | Gt |

Naive          Naive challenge

Pre-F          Gt          Pre-F+Gt

FI RSV          Live RSV

Naive    Naive challenge    FI RSV    Live RSV

Pre-F VLP    G VLP    Pre-F+G VLP

SEQUENCE LISTING

Sequence total quantity: 14
SEQ ID NO: 1              moltype = DNA   length = 897
FEATURE                   Location/Qualifiers
source                    1..897
                          mol_type = other DNA
                          organism = synthetic construct
SEQUENCE: 1
atgtcgaaaa acaaggacca aaggacggcg aaaacgctgg agaggacctg ggatacgctg    60
aaccacctgc tcttcattag tagttgcctg tacaagctga acctgaagtc tgtggctcag   120
atcaccctgt caatcctggc catgatcatc tctacttcac tgatcatcgc tgccatcatc   180
ttcatcgctt ccgccaacca caaggtcacc ccaaccactg ctatcatcca ggacgccact   240
agccagatca agaacaccac tccaacttac ctgacccaga accctcagct gggaatctcc   300
cctagcaacc cctctgagat cacctcacag atcaccacta tcctggcttc caccactcct   360
ggtgtgaagt ccactctgca gagcaccact gtcaagacca agaacaccac taccactcag   420
actcagccat ctaagcctac cactaagcag cgccagaaca agcctccctc aaagcccaac   480
aacgacttcc acttcgaagt gttcaacttc gtccctgct ccatctgctc taacaaccca   540
acctgctggg ccatctgcaa gcgtatcccc aacaagaagc caggcaagaa gaccactacc   600
aagcctacta agaagcccac cctgaagact accaagaagg acccaaagcc tcagactacc   660
aagtctaagg aggtgccaac taccaagcct actgaggaac ccaccatcaa cactaccaag   720
accaacatca tcactaccct gctgacttcc aacactaccg gtaaccctga gctgacctcc   780
cagatggaaa ctttccacag cacctccagc gaaggcaacc cctctccatc acaggtcagc   840
acaacgagcg aataccctc acagccaagt tctccaccaa acacacccag acagtaa       897

SEQ ID NO: 2              moltype = DNA   length = 261
FEATURE                   Location/Qualifiers
source                    1..261
                          mol_type = other DNA
                          organism = synthetic construct
SEQUENCE: 2
atgtccaaaa acaaggacca acgcaccgct aagacattag aaaggacctg ggacactctc    60
aatcatttat tattcatatc atcgtgctta tataagttaa atcttaaatc tgtagcacaa   120
atcacattat ccattctggc aatgataatc tcaacttcac ttataattgc agccatcata   180
ttcatagcct cggcaaacca caaagtcaca ccaacaactg caatcataca agatgcaaca   240
agccagatca agaacacaac c                                             261

SEQ ID NO: 3              moltype = DNA   length = 111
FEATURE                   Location/Qualifiers
source                    1..111
                          mol_type = other DNA
                          organism = synthetic construct
SEQUENCE: 3
ctcaacttca cttataattg cagccatcat attcatagcc tcggcaaacc acaaagtcac    60
accaacaact gcaatcatac aagatgcaac aagccagatc aagaacacaa c            111

SEQ ID NO: 4              moltype = DNA   length = 384
FEATURE                   Location/Qualifiers
source                    1..384
                          mol_type = other DNA
                          organism = synthetic construct
SEQUENCE: 4
atgtccaaaa acaaggacca acgcaccgct aagacattag aaaggacctg ggacactctc    60
aatcatttat tattcatatc atcgtgctta tataagttaa atcttaaatc tgtagcacaa   120
atcacattat ccattctggc aatgataatc tcaacttcac ttataattgc agccatcata   180
ttcatagcct cggcaaacca caaagtcaca ccaacaactg caatcataca agatgcaaca   240
agccagatca agaacacaac cggcggcggc ggcctcaact tcacttataa ttgcagccat   300
catattcata gcctcggcaa accacaaagt cacaccaaca actgcaatca tacaagatgc   360
aacaagccag atcaagaaca caac                                          384

SEQ ID NO: 5              moltype = DNA   length = 501
FEATURE                   Location/Qualifiers
source                    1..501
                          mol_type = other DNA
                          organism = synthetic construct
SEQUENCE: 5
atgtccaaaa acaaggacca acgcaccgct aagacattag aaaggacctg ggacactctc    60
aatcatttat tattcatatc atcgtgctta tataagttaa atcttaaatc tgtagcacaa   120
atcacattat ccattctggc aatgataatc tcaacttcac ttataattgc agccatcata   180
ttcatagcct cggcaaacca caaagtcaca ccaacaactg caatcataca agatgcaaca   240
agccagatca agaacacaac cggcggcggc tcaacttcac ttataattgc agccatcata   300
ttcatagcct cggcaaacca caaagtcaca ccaacaactg caatcataca agatgcaaca   360
agccagatca agaacacaac cggccagatt ctggcgatct actcaactgt cgccagttca   420
ctggtgcttt tggtctccct gggggcaatc agtttctgga tgtgttctaa tggatctttg   480
cagtgcagaa tatgcatctg a                                             501

SEQ ID NO: 6              moltype = DNA   length = 1695
FEATURE                   Location/Qualifiers
source                    1..1695
                          mol_type = other DNA

```
                          organism = synthetic construct
SEQUENCE: 6
atggagttgc tcatcctcaa ggctaacgct attactacta tcctcaccgc cgtcacattc    60
tgcttcgctt cgggacaaaa catcaccgag gagttctacc agtctacttg ctcagctgtc   120
tccaagggat acctgtccgc cctgcgcacc ggttggtaca ctagcgtgat caccatcgag   180
ctgtctaaca tcaaggaaaa caagtgcaac ggtactgacg ccaaggtcaa gctgatcaag   240
caggagctgg acaagtacaa gaacgctgtg accgaactgc agctgctgat gcagtcaacc   300
ccagctacta caacagggc ccgccgtgag ctgcctagat tcatgaacta caccctgaac   360
aacgccaaga agaccaacgt cactctgtcc aagaagcaga agcagcaggc tatcgcctca   420
ggagtggctg tctccaaggt cctgcacctg gagggcgaag tgaacaagat caagagcgct   480
ctgctgtcta ctaacaaggc cgtggtgtcc ctgtccaacg tgtgtcagt cctgacctcc   540
aaggtgctgg acctgaagaa ctacatcgac aagcagctgc tgcccatcgt caacaagcag   600
agctgctcta tctcaaacat cgagactgtg atcgagttcc agcagaagaa caaccgcctg   660
ctggagatca cccgcgagtt ctcagtgaac gccggcgtca ccatcctgt gtccacttac   720
atgctgacca acagcgagct gctgtctctg atcaacgaca tgcccatcac caacgaccag   780
aagaagctga tgagcaacaa cgtgcagatc gtccgtcagc agtcctacag catcatgtct   840
atcatcaagg aggaagtcct ggcttacgtg gtccagctgc cactgtacgg agtgatcgac   900
actccttgct ggaagctgca caccagcccc ctgtgcacca ctaacactaa ggaaggttct   960
aacatctgcc tgaccaggac tgacagaggt tggtactgcg acaacgctgg ctctgtgtca  1020
ttcttcccac aggccgaaac ctgcaaggtc cagagcaaca gggtgttctg cgacactatg  1080
aacagcctga ccctgccctc tgaagtcaac ctgtgcaacg tggacatctt caacccaaag  1140
tacgactgca gatcatgac cagcaagact gacgtctcca gctctgtgat cacttcactg  1200
ggagctatcg tgtcctgcta cggcaagacc aagtgcactg cctctaacaa gaacagaggc  1260
atcatcaaga ccttctcaaa cggatgcgac tacgtctcca caagggcgt ggacactgtg  1320
tcagtcggaa acacccctgta ctacgtcaac aagcaggagg gcaagtccct gtacgtgaag  1380
ggcgaaccta tcatcaactt ctacgaccct ctggtcttcc ccagcgacga gttcgacgct  1440
tccatcagcc aggtgaacga aaagatcaac cagagcctgg ccttcatccg caagtctgac  1500
gagctgctgc acaacgtcaa cgctggcaag tctaccacta acatcatgat caccactatc  1560
atcatcgtga tcatcgtcat cctgctgtca ctgatcgctg tgggactgct gctgtactgc  1620
aaggcccgtt ccacccctgt gactctctcc aaggaccaac tctcgggaat caacaacatt  1680
gcgttcagta actaa                                                    1695

SEQ ID NO: 7                moltype = DNA  length = 771
FEATURE                     Location/Qualifiers
source                      1..771
                            mol_type = other DNA
                            organism = synthetic construct
SEQUENCE: 7
atggaaacat acgtgaacaa gcttcacgaa ggctccacat acacagctgc tgttcaatac    60
aatgtcttag aaaaagacga tgaccctgca tcacttacaa tatgggtgcc catgttccaa   120
tcatctatgc cagcagattt acttataaaa gaactagcta atgtcaacat actagtgaaa   180
caaatatcca cacccaaggg accttcacta agagtcatga taaactcaag aagtgcagtg   240
ctagcacaaa tgcccagcaa atttaccata tgcgctaatg tgtccttgga tgaaagaagc   300
aaactagcat atgatgtaac cacacccctgt gaaatcaagg catgtagtct aacatgccta   360
aaatcaaaaa atatgttgac tacagttaaa gatctcacta tgaagacact caacccctaca   420
catgatatta ttgctttatg tgaatttgaa aacatagtaa catcaaaaaa agtcataata   480
ccaacatacc taagatccat cagtgtcaga aataaagatc tgaaaatata   540
acaaccactg aattcaaaaa tgctatcaca aatgcaaaaa tcatccctta ctcaggatta   600
ctattagtca tcacagtgac tgacaacaaa ggagcattca aatacataaa gccacaaagt   660
caattcatag tagatcttgg agcttaccta gaaaaagaaa gtatatatta tgttaccaca   720
aattggaagc acacagctac acgatttgca atcaaaccca tggaagatta a            771

SEQ ID NO: 8                moltype = AA  length = 298
FEATURE                     Location/Qualifiers
source                      1..298
                            mol_type = protein
                            organism = synthetic construct
SEQUENCE: 8
MSKNKDQRTA KTLERTWDTL NHLLFISSCL YKLNLKSVAQ ITLSILAMII STSLIIAAII    60
FIASANHKVT PTTAIIQDAT SQIKNTTPTY LTQNPQLGIS PSNPSEITSQ ITTILASTTP   120
GVKSTLQSTT VKTKNTTTTQ TQPSKPTTKQ RQNKPPSKPN NDFPHFEVFNF VPCSICSNNP   180
TCWAICKRIP NKKPGKKTTT KPTKKPTLKT TKKDPKPQTT KSKEVPTTKP TEEPTINTTK   240
TNIITTLLTS NTTGNPELTS QMETFHSTSS EGNPSPSQVS TTSEYPSQPS SPPNTPRQ    298

SEQ ID NO: 9                moltype = AA  length = 87
FEATURE                     Location/Qualifiers
source                      1..87
                            mol_type = protein
                            organism = synthetic construct
SEQUENCE: 9
MSKNKDQRTA KTLERTWDTL NHLLFISSCL YKLNLKSVAQ ITLSILAMII STSLIIAAII    60
FIASANHKVT PTTAIIQDAT SQIKNTT                                        87

SEQ ID NO: 10               moltype = AA  length = 37
FEATURE                     Location/Qualifiers
source                      1..37
                            mol_type = protein
                            organism = synthetic construct
SEQUENCE: 10
```

-continued

```
LNFTYNCSHH IHSLGKPQSH TNNCNHTRCN KPDQEHN                          37

SEQ ID NO: 11              moltype = AA   length = 166
FEATURE                    Location/Qualifiers
source                     1..166
                           mol_type = protein
                           organism = synthetic construct
SEQUENCE: 11
MSKNKDQRTA KTLERTWDTL NHLLFISSCL YKLNLKSVAQ ITLSILAMII STSLIIAAII  60
FIASANHKVT PTTAIIQDAT SQIKNTTGGG GLNFTYNCSH HIHSLGKPQS HTNNCNHTRC  120
NKPDQEHNQI LAIYSTVASS LVLLVSLGAI SFWMCSNGSL QCRICI                 166

SEQ ID NO: 12              moltype = AA   length = 564
FEATURE                    Location/Qualifiers
source                     1..564
                           mol_type = protein
                           organism = synthetic construct
SEQUENCE: 12
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKQKQQAIAS GVAVSKVLHL EGEVNKIKSA LLSTNKAVVS LSNGVSVLTS  180
KVLDLKNYID KQLLPIVNKQ SCSISNIETV IEFQQKNNRL LEITREFSVN AGVTTPVSTY  240
MLTNSELLSL INDMPITNDQ KKLMSNNVQI VRQQSYSIMS IIKEEVLAYV VQLPLYGVID  300
TPCWKLHTSP LCTTNTKEGS NICLTRTDRG WYCDNAGSVS FFPQAETCKV QSNRVFCDTM  360
NSLTLPSEVN LCNVDIFNPK YDCKIMTSKT DVSSSVITSL GAIVSCYGKT KCTASNKNRG  420
IIKTFSNGCD YVSNKGVDTV SVGNTLYYVN KQEGKSLYVK GEPIINFYDP LVFPSDEFDA  480
SISQVNEKIN QSLAFIRKSD ELLHNVNAGK STTNIMITTI IIVIIVILLS LIAVGLLLYC  540
KARSTPVTLS KDQLSGINNI AFSN                                        564

SEQ ID NO: 13              moltype = AA   length = 252
FEATURE                    Location/Qualifiers
source                     1..252
                           mol_type = protein
                           organism = synthetic construct
SEQUENCE: 13
MSLLTEVETY VLSIIPSGPL KAEIAQRLED VFAGKNTDLE VLMEWLKTRP ILSPLTKGIL  60
GFVFTLTVPS ERGLQRRRFV QNALNGNGDP NNMDKAVKLY RKLKREITFH GAKEISLSYS  120
AGALASCMGL IYNRMGAVTT EVAFGLVCAT CEQIADSQHR SHRQMVTTTN PLIRHENRMV  180
LASTTAKAME QMAGSSEQAA EAMEVASQAR QMVQAMRTIG THPSSSAGLK NDLLENLQAY  240
QKRMGVQMQR FK                                                     252

SEQ ID NO: 14              moltype = AA   length = 256
FEATURE                    Location/Qualifiers
source                     1..256
                           mol_type = protein
                           organism = synthetic construct
SEQUENCE: 14
METYVNKLHE GSTYTAAVQY NVLEKDDDPA SLTIWVPMFQ SSMPADLLIK ELANVNILVK  60
QISTPKGPSL RVMINSRSAV LAQMPSKFTI CANVSLDERS KLAYDVTTPC EIKACSLTCL  120
KSKNMLTTVK DLTMKTLNPT HDIIALCEFE NIVTSKKVII PTYLRSISVR NKDLNTLENI  180
TTTEFKNAIT NAKIIPYSGL LLVITVTDNK GAFKYIKPQS QFIVDLGAYL EKESIYYVTT  240
NWKHTATRFA IKPMED                                                 256
```

VIRUS-LIKE PARTICLES CONTAINING RSV ANTIGEN PROTEIN AND VACCINES USING THE SAME

TECHNICAL FIELD

This application claims priority to Korean Patent Application No. 10-2021-0178199, filed on Dec. 4, 2021.

The present disclosure relates to a virus-like particle including an RSV antigen protein and a vaccine using the same.

REFERENCE TO AN ELECTRONIC SEQUENCE LISTING

The contents of the electronic sequence listing (2022-11-03_SequenceListing.xml; Size: 19,458 bytes; and Date of Creation: Nov. 3, 2022) is herein incorporated by reference in its entirety.

BACKGROUND

The scientific name of respiratory syncytial virus (RSV) is *Human orthopneumovirus*. RSV is a negative-sense single-stranded RNA virus with a lipid envelope. In the lipid envelope of RSV, there are G proteins and F proteins, which are surface proteins. G proteins and F proteins are the two major surface proteins involved in viral attachment and early stages of infection, and these proteins are major targets of antibodies. The G protein is a glycoprotein and plays a role in attaching the virus to the ciliary cells of the host airway. The F protein is an abbreviation of a fusion protein and it serves to fuse the cell membranes of a virus and a host to form a syncytium. The F protein has several forms. Before binding to a host cell, the F protein is called preF (prefusion state). The preF protein exists in a trimeric form and includes an antigenic site $\Psi$. When RSV binds to a host cell, the preF loses $\Psi$, undergoes a change in its shape, is inserted into the host cell membrane, and induces a fusion of the virus with the host cell membrane. The F protein which has undergone a conformational change becomes stable and is in a long postfusion state (PostF).

To date, there is no licensed vaccine to prevent RSV infection. The RSV vaccines reported to the academic community are not highly immunogenic and have a side effect that induces an inflammatory response in the lungs; therefore, they have not been commercialized.

Prior Document

Patent Document (Patent Document 1) Korean Patent Application Publication No. 10-1862137 (May 1, 2017)

Non-Patent Document (Non-Patent Document 1) Virus-like particle vaccines expressing *Toxoplasma gondii rhoptry protein* 18 and microneme protein 8 provide enhanced protection. Vaccine 2018, 36, 5692-5700

SUMMARY

According to a specific embodiment, the present disclosure provides a virus-like particle (VLP), which includes influenza M1, RSV-derived preF, and chimeric protein comprising all or some residue of RSV-derived G proteins, and an RSV vaccine using the same.

An aspect of the present disclosure provides a respiratory syncytial virus (RSV)-like particle, which includes: a core consisting of an influenza virus matrix protein 1 (M1); and an antigenic protein displayed on the surface of the core, wherein the antigen protein includes a preF protein derived from RSV consisting of an amino acid sequence of SEQ ID NO: 12.

The RSV-derived preF protein is a codon-optimized sequence based on the sequence of GenBank: MN125707.1, and the immunization effect can be significantly enhanced when used as a VLP in combination with M1 than when used alone.

In a specific embodiment, the antigen protein may further include an RSV-derived G protein; or a chimeric protein, which includes a first tandem sequence consisting of an amino acid sequence of SEQ ID NO: 9 and a second tandem sequence consisting of an amino acid sequence of SEQ ID NO: 10.

The present inventors prepared various VLPs by combining RSV-M or influenza M1 as a core and RSV-preF, RSV-G, and RSV-Gt as an antigen protein; infected VLP-immunized mice with RSV to determine the viral titer and the degree of pulmonary inflammatory response. As a result, they found that the VLPs in which M1 core protein and antigenic protein were combined increased the immunization effect against RSV and reduced the inflammatory side effects of the lungs, that the immunization effect of VLPs in which RSV-preF was combined with M1 was significantly superior to that of VLPs in which RSV-preF was used alone, and that the effect was further enhanced when RSV-preF and RSV-G or Gt were combined.

Additionally, the present inventors found that in the process of producing a chimeric protein including a part of the nucleotide sequence of G protein, if the $151^{st}$ to the $261^{st}$ and the $151^{st}$ to the 260th nucleotides of the nucleotide sequence encoding the G protein are used, the expression did not go smoothly, whereas when the nucleotides from the $150^{th}$ to the $260^{th}$ of the nucleotide sequence were used, the expression went smoothly. Additionally, the protein expressed from the nucleotide sequence from the $150^{th}$ to the $260^{th}$ nucleotides consists of an amino acid sequence different from the original G protein due to changes in triplet codons, and that it has an excellent immunization effect of the modified protein.

The virus-like particle (VLP) is a non-infectious particle because it includes a protein of a virus but does not include a genetic material. Virus-like particles can be synthesized by individual expression and self-assembly of viral structural proteins. The influenza virus matrix protein 1 (M1) is a structural protein of the influenza virus, and it refers to a matrix protein that forms a coat inside the envelope of the influenza virus. According to an embodiment, the M1 protein can be used as a structural protein of a virus-like particle. The M1 protein may consist of the amino acid sequence of SEQ ID NO: 13.

The antigen protein refers to a protein that can be recognized by B cells or T cells to induce an immune activation response.

According to an embodiment, the G protein may consist of the amino acid sequence of SEQ ID NO: 8.

According to an embodiment, the chimeric protein may be one in which a transmembrane domain (TM) and a cytoplasmic tail (CT) of influenza hemagglutinin are bound. TM-CT may be expressed from a sequence corresponding to the $385^{th}$ to the $501^{st}$ nucleotides in SEQ ID NO: 5.

According to an embodiment, the chimeric protein may be one in which a first tandem sequence and a second tandem sequence are linked by a linker. The linker is not particularly limited, and may be, for example, a linker including four consecutive glycines (Gly).

According to an embodiment, the chimeric protein may consist of an amino acid sequence of SEQ ID NO: 11. In the amino acid sequence of SEQ ID NO: 11, the sequence from the $1^{st}$ to the $87^{th}$ nucleotides is a first tandem sequence; the sequence from the $88^{th}$ to the $91^{st}$ nucleotides is a 4x Gly linker; the sequence from the $92^{nd}$ to the $128^{th}$ nucleotides is a second tandem sequence; and the sequence from the $129^{th}$ to the $166^{th}$ nucleotides is a TM-CT sequence.

The virus-like particle may be prepared by a method known to those skilled in the art, for example, it may be prepared by a baculovirus expression system.

Another aspect of the present disclosure provides a vaccine composition for preventing or treating RSV infection including the RSV virus-like particle as an active ingredient.

According to an embodiment, it was confirmed that the mice immunized by inoculation with the RSV virus-like particles had very low viral titers and significantly lower inflammatory side effects even when challenged with RSV virus.

According to a specific embodiment, the composition may further include an adjuvant. The adjuvant refers to a substance or composition that is added to vaccines or pharmaceutically active ingredients to increase or affect an immune response. The adjuvant may be selected from the group consisting of, for example, aluminum salts, toll-like receptor (TLR) agonists, monophosphoryl lipid A (MLA), synthetic lipid A, lipid A mimetics or analogues, MLA derivatives, cytokines, saponins, muramyl dipeptide (MDP) derivatives, CpG oligos, lipopolysaccharides (LPS) of Gram-negative bacteria, polyphosphazenes, emulsions, virosomes, cacliat, poly(lactide-co-glycolide) (PLG) microparticles, poloxamer particles, microparticles, liposomes, complete Freund's adjuvant (CFA), and incomplete Freund's adjuvant (IFA), and as the aluminum salt, aluminum hydroxide or aluminum phosphate may be used, but is not particularly limited thereto.

The vaccine composition may be used by formulating it in the form of oral dosage forms (e.g., powders, granules, tablets, capsules, suspensions, emulsions, syrups, aerosols, etc.) and sterile injection solutions according to conventional methods. When formulating, the vaccine composition may be prepared using commonly used diluents or excipients (e.g., fillers, extenders, binders, wetting agents, disintegrants, surfactants, etc.). Solid preparations for oral administration may include tablets, pills, powders, granules, capsules, etc. These solid preparations may be prepared by mixing at least one excipient, for example, starch, calcium carbonate, sucrose or lactose, gelatin, etc. with the lecithin-like emulsifier. In addition to simple excipients, lubricants (e.g., magnesium styrate and talc) may also be used. As liquid preparations for oral administration, suspensions, liquid solutions for internal use, emulsions, syrups, etc. may be used; and in addition to water and liquid paraffin, which are commonly used simple diluents, various excipients (e.g., wetting agents, sweetening agents, fragrances, preservatives, etc.) may be included. Preparations for parenteral administration include sterile aqueous solutions, non-aqueous agents, suspensions, emulsions, and lyophilized agents. As the non-aqueous preparation and suspension, propylene glycol, polyethylene glycol, vegetable oils (e.g., olive oil), injectable esters (e.g., ethyl oleate), etc. may be used.

The administration route of the vaccine composition is not particularly limited, but the vaccine composition may be administered, for example, orally or parenterally, and specifically, may be administered via oral, intravenous, intramuscular, intraarterial, intramedullary, intrathecal, intracardiac, transdermal, subcutaneous, intraperitoneal, intranasal, intestinal, topical, sublingual, or rectal administration route. Parenteral administration may include subcutaneous, intradermal, intravenous, intramuscular, intraarticular, intrasynovial, intrasternal, intrathecal, intralesional, and intracranial injections. The administration dose of the vaccine composition may be selected in consideration of the individual's age, weight, sex, physical condition, etc. The amount required to induce an immune response in an individual without any side effects may vary depending on the presence of VLPs and other components used as immunogens, which may be determined by methods known to those skilled in the art.

Another aspect of the present disclosure provides a method for preparing an RSV virus-like particle, which includes co-infecting an insect cell with a first recombinant baculovirus expressing influenza virus matrix protein 1 (M1); and a second recombinant baculovirus expressing an RSV-derived G protein; and culturing the co-infected insect cell and purifying virus-like particles.

According to a specific embodiment, the step of co-infecting may be to co-infect the insect cell with the first recombinant baculovirus; the second recombinant baculovirus; and a third recombinant baculovirus which expresses the RSV-derived G protein or a chimeric protein including a first tandem sequence consisting of an amino acid sequence of SEQ ID NO: 9 and a second tandem sequence consisting of an amino acid sequence of SEQ ID NO: 10.

Advantageous Effects

A VLP vaccine according to an embodiment has an excellent immune effect against RSV and has an effect that suppresses a pulmonary inflammatory response by combining influenza M1 and RSV-derived preF.

A VLP vaccine according to an embodiment can further improve the immune effect and the effect of suppressing a pulmonary inflammatory response by combining all of influenza M1, RSV-derived preF, and RSV-derived G protein or a modified chimeric protein thereof.

BRIEF DESCRIPTION OF THE DRAWINGS

FIG. 1 shows an RSV-Gt tandem sequence in which the TM-CT sequence of influenza hemagglutinin and the nucleotide sequence of the $1^{st}$ to the $261^{st}$ nucleotides and the nucleotide sequence of the $150^{th}$ to the $260^{th}$ nucleotides of the nucleotide sequence expressing G protein of RSV are linked.

FIG. 2 shows TEM images of RSV-preF VLPs (Pre-F VLPs), RSV-preF+G (Pre-F+G VLPs), and RSV-preF+Gt (Pre-F+Gt VLPs) prepared according to an embodiment.

FIG. 3 shows the results of a total of 5 VLPs (i.e., (1) RSV-preF+M1 VLP, (2) RSV-preF+RSV-G+M1 VLP, (3) RSV-preF+RSV-Gt+M1 VLP, (4) RSV-G+M1 VLP, (5) RSV-Gt+M1 VLP VLP) confirmed by Western blot.

DETAILED DESCRIPTION

Figure 4A:
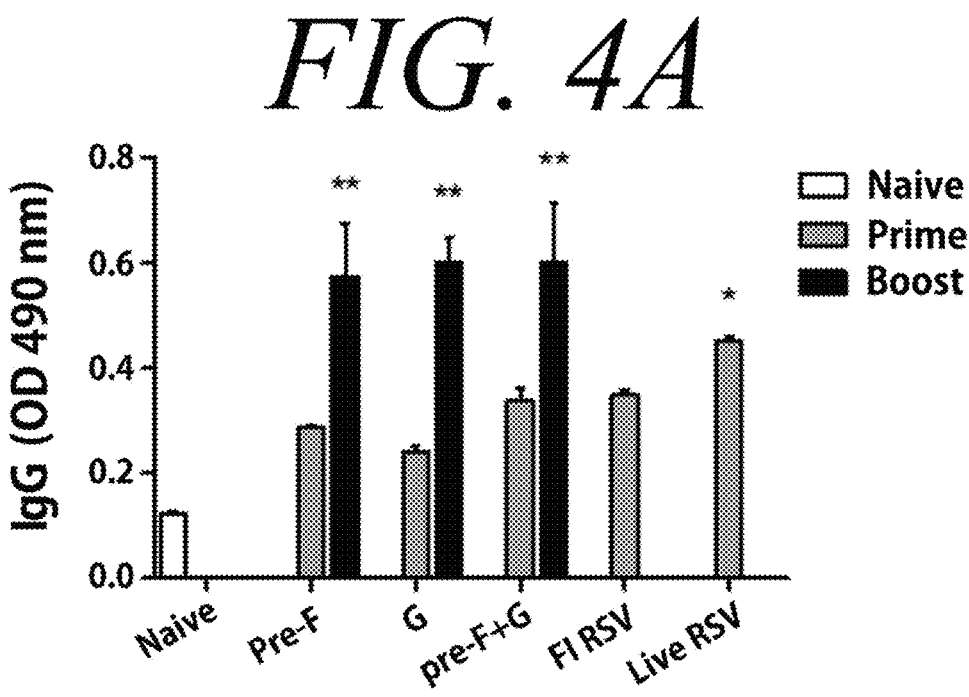
FIG. 4A shows the result confirming the IgG titers of the groups inoculated with the VLP vaccine prepared according to Example 2-1.

Hereinafter, one or more specific embodiments will be described in more detail through Examples. However, these Examples are for illustrative purposes of one or more embodiments, and the scope of the present invention is not limited to these Examples.

Example 1: Preparation of VLPs in which RSV-preF, RSV-G, and RSV-Gtare Combined 1-1. Preparation of VLP Including Influenza M1 as Core Protein As a VLP including influenza M1 as a core protein, a total of five VLPs (i.e., (1) RSV-preF+M1 VLP, (2) RSV-preF+RSV-G+M1 VLP, (3) RSV-preF+RSV-Gt+M1 VLP, (4) RSV-G+M1, and (5) RSV-Gt+M1 VLP) were prepared.

RSV-G, which is a full-length G protein of RSV strain A2, is a protein expressed from a codon-optimized nucleotide sequence.

RSV-Gt is a chimeric protein expressed from a gene construct (SEQ ID NO: 5), in which in the G protein of RSV strain A2, a nucleotide sequence from the $1^{st}$ nucleotide to the $261^{st}$ nucleotide of (a first tandem sequence, SEQ ID NO: 2) and a nucleotide sequence from the $150^{th}$ nucleotide to the $260^{th}$ nucleotide (a first tandem sequence, SEQ ID NO: 2) are connected to a 4× Gly linker (a tandem sequence, see SEQ ID NO: 4), and at the 3' end, it is linked to TM-CT (transmembrane domain CT), which is a protein of a transmembrane domain (TM) and a cytoplasmic tail (CT) of influenza hemagglutinin (HA) (see FIG. 1). Although the nucleotide sequence of the second tandem is derived from the nucleotide sequence from the $150^{th}$ to the $260^{th}$ nucleotides of RSV-G, the protein expressed therefrom differs from the sequence of the G protein due to the change in the triplet code. The present inventors linked, as the second tandem sequence, a nucleotide sequence from the $151^{st}$ to the $261^{st}$ nucleotides or a nucleotide sequence from the $151^{st}$ to the $260^{th}$ nucleotides of the G protein, but the protein expression of both sequences was not smooth. However, it was confirmed that in the case of a nucleotide sequence where the $150^{th}$ to the $260^{th}$ nucleotides were linked, the protein expression was smooth and the immune induction response was also excellent.

RSV-preF, which is an F protein in the form of RSV strain A2, is a protein expressed from a nucleotide sequence that is codon-optimized based on the nucleotide sequences of GenBank: FJ614814.1.

The codon-optimized nucleotide sequences for the expression of RSV-G and RSV-PReF were provided by Genescript Biotech Corp.

The RSV-G coding nucleotide sequence (SEQ ID NO: 1), RSV-Gt coding nucleotide sequence (SEQ ID NO: 5), and RSV-preF coding nucleotide sequence (SEQ ID NO: 6) were amplified by PCR. Each of the amplified genes was introduced into the pFastBac vector to prepare a cloning vector and digested with restriction enzymes to confirm whether the nucleic acid sequence was introduced. The nucleic acid sequence of the introduced gene was confirmed by the DNA sequencing method (Eurofins MWG Operon).

DH10Bac™ competent cells were transformed with the cloning vector. Transpositioned recombinant bacmid DNA was isolated from the transformed DH10Bac cells. Sf9 cells were transfected with the recombinant bacmid DNA using Cellfectin II reagent (Invitrogen). Recombinant baculovirus (rBV) expressing full-length (RSV-G), RSV-Gt, or RSV-preF was produced using the transfected Sf cells.

One or more rBVs expressing RSV-G (full length), RSV-Gt, and RSV-preF, and influenza M1-expressing rBV were co-transfected into Sf9 cells to produce the five VLPs described above. The co-infection ratio was 1:3 to 1:4 for M1:preF, M1:G, and M1:Gt, and 1:2.5:2.5 for M1:preF:G, and Gt. The methods for producing influenza M1-expressing rBV and co-transfection are described in "Virus-like particle vaccines expressing *Toxoplasma gondii* rhoptry protein 18 and microneme protein 8 provide enhanced protection. Vaccine 2018, 36, 5692-5700".

The co-transfected Sf9 cells were incubated at 27° C. and 140 rpm for three days. The transfected Sf9 cell culture was centrifuged at 4° C. and 6,000 RPM for 30 minutes, and the supernatant was collected. The supernatant was ultracentrifuged at 30,000 RPM and 4° C. for 1 hour, and the pellets containing VLP particles were collected. PBS was added to the pellet and resuspended.

The resuspension was placed on a discontinuous sucrose gradient (60% 2 mL/30% 4 mL/15% 4 mL) and ultracentrifuged under 30,000 RPM, 4° C., and one hour conditions, and the bands formed between the 60% layer and the 30% layer were collected. The collected bands were resuspended in PBS and ultracentrifuged under 30,000 RPM, 4° C., and 30 minutes conditions to obtain a pellet containing purified VLPs. The pellet was resuspended in PBS and used in the experiment.

The images of each of RSV-preF, RSV-preF+G, and RSV-preF+Gt introduced into the VLP were confirmed by TEM and are shown in FIG. 2.

To confirm whether RSV-G, RSV-Gt, and RSV-preF were introduced into the VLP, Western blot was performed using an antibody for each. According to FIG. 3, it was confirmed that in all of the five kinds of VLPs, the RSV-preF, RSV-G, RSV-Gt, and M1 included therein were expressed and that the simultaneous expression of RSV-Gt or RSV-G and preF was excellent.

1-2. Preparation of VLPs Including RSV M as Core Protein

VLPs including the RSV M core protein were prepared in the same manner as in Example 1-1, except that the rBV that expresses the RSV M protein of SEQ ID NO: 14 using the RSV-M nucleotide sequence of SEQ ID NO: 7 instead of the rBV that expresses M1 in the Example.

Example 2: Immunization and Challenge Infection 2-1. Vaccine Dose of 120 μg

Mice immunized with influenza M1-based VLPs (BALB/c) were infected with RSV A2 virus. As vaccines, RSV-PreF VLPs, RSV-G VLPs, and RSV-F+G VLPs prepared in the same manner as in Example 1 were used.

The mice were subjected to prime vaccination with 50 μL of PBS including 120 μg of VLPs by the intranasal route (i.n.), and after 4 weeks of the vaccination, the mice were subjected to boost vaccination with 50 μL of PBS including 120 μg of VLPs. Five weeks after the boost vaccination, the mice were subjected to challenge infection with 50 μL of PBS including RSV A2 virus (4×10⁰ pfu) by the intranasal route (i.n.), and the lungs of the mice were obtained five days after the challenge infection.

2-2. Vaccine Dose of 100 μg

As vaccines, RSV-PreF VLPs, RSV-Gt VLPs, and RSV-PreF+Gt VLPs prepared in the same manner as in Example 1 were used, and the mice were subjected to vaccination and challenge infection in the same manner as in Example 2-1, except that the vaccination dose was 100 μg.

2-3. Vaccine Dose of 80 μg

As vaccines, RSV-PreF VLPs, RSV-PreF+G VLPs, and RSV-PreF+Gt VLPs prepared in the same manner as in Example 1 were used, and the mice were subjected to vaccination and challenge infection in the same manner as in Example 2-1, except that the vaccination dose was 80 g.

Example 3: Antibody IgG Response of Influenza M1-Based VLPs

In Examples 2-1 and 2-2, mice sera were collected by retro-orbital plexus puncture before and after the primary vaccination and boost vaccination. The sera were centrifuged at 3,000 rpm at 4° C. for 10 minutes.

Figure 4B:
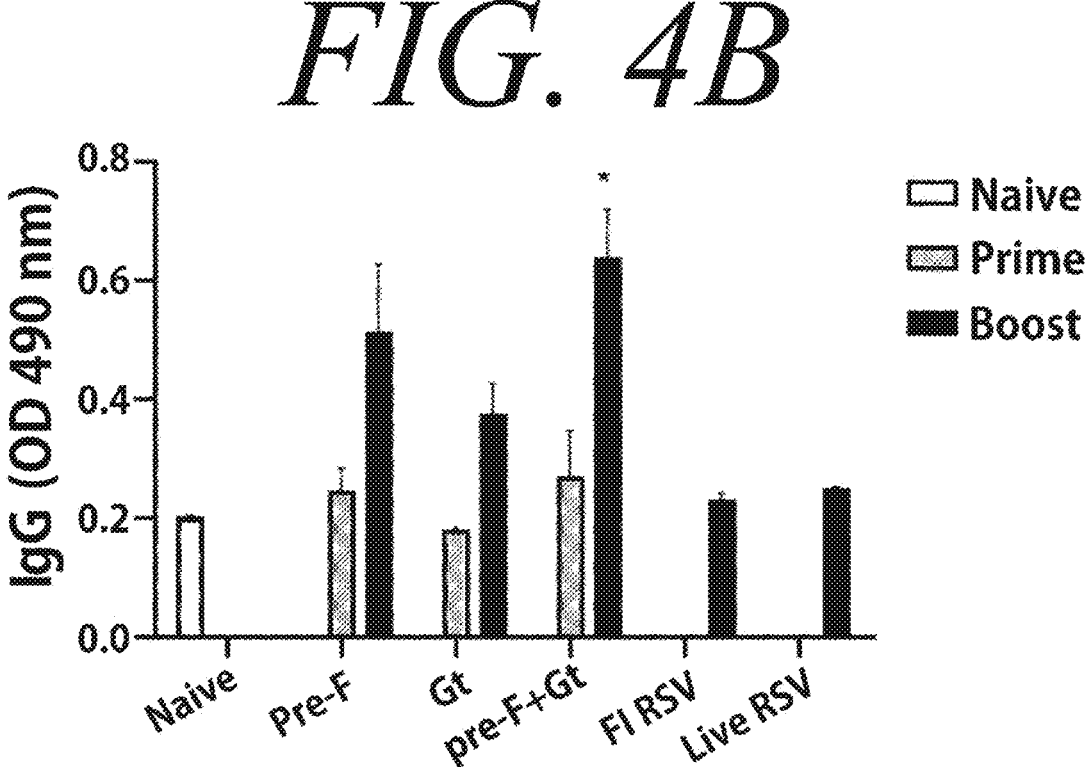
FIG. 4B shows the results confirming the IgG titers of the groups inoculated with the VLP vaccine prepared according to Example 2-2.

After coating the formalin-inactivated RSV virus (4 μg/mL, 100 μL/well) on a 96 well plate, the 96 well plate was blocked by treating with 5% skim milk at 100 μl/well at 37° C. for one hour. The collected sera were diluted 100-fold with PBS-T as a primary reaction antibody, treated at 100 μL/well, and reacted at 37° C. for two hours. As a secondary antibody, a horseradish peroxidase (HRP)-conjugated IgG antibody was diluted 2,000-fold with PBS-T, treated at 100 μL/well, and reacted at 37° C. for one hour. OPD substrate buffer was treated at 100 L/well to the reaction material to confirm color development (color development was confirmed at 490 nm or 450 nm in an ELISA reader), and the reaction was stopped by treating with 2 N sulfuric acid at 50 μL/well. According to FIG. 4A, the IgG antibody titers of the groups vaccinated with the VLP vaccines according to Example 2-1 were significantly increased compared to the non-vaccinated group. In particular, the sera from obtained from the mice subjected to the secondary boost showed a high level of IgG antibody response. According to FIG. 4B, in the groups vaccinated with the VLP vaccines according to Example 2-2, the IgG antibody titers according to the secondary boost were significantly increased compared to the non-vaccinated group.

Example 4: Neutralizing Activity of Influenza M1-Based VLP Virus Against RSV a Virus Mice sera were collected by retro-orbital plexus puncture from before and after the primary vaccination and boost vaccination in Example 2 above. The collected mouse sera were subjected to 100, 300, 900, and 2,700-fold dilutions (Example 2-1), 50, 250, 1,250, and 6,250-fold dilutions (Example 2-2), and 50, 250, 500, and 1,000-fold dilutions (Example 2-3) in PBS), and incubated in a 56° C. water bath for 30 minutes.

100 μL of each of the incubated sera and 100 μL of each of the RSV A viruses (100-300 pfu) were mixed and incubated at 37° C. for one hour. The incubated samples were dispensed at 200 μL/well in a 24-well plate in which Hep-2 cells were dispensed, and incubated at 37° C. for one hour. After removing the samples, 1 mL/well of overlay media (a 1:1 mixture of 1% noble agar and DMEM media)

was dispensed and incubated at 37° C. for 3 to 4 days. After removing the overlay media, 200 μL/well of a fixative solution (acetone and methanol=1:1) was injected into the cells and fixed at room temperature for 20 minutes, 200 μL/well of a primary antibody (an anti-RSV Fusion monoclonal Ab (1:2000)) and a secondary antibody (an IgG-HRP conjugated Ab (1:3000)) were treated at room temperature for one hour. Thereafter, the neutralizing activity was confirmed by treating with 200 μL/well of DAB colorant at room temperature for 20 to 30 minutes.

Figure 5A:
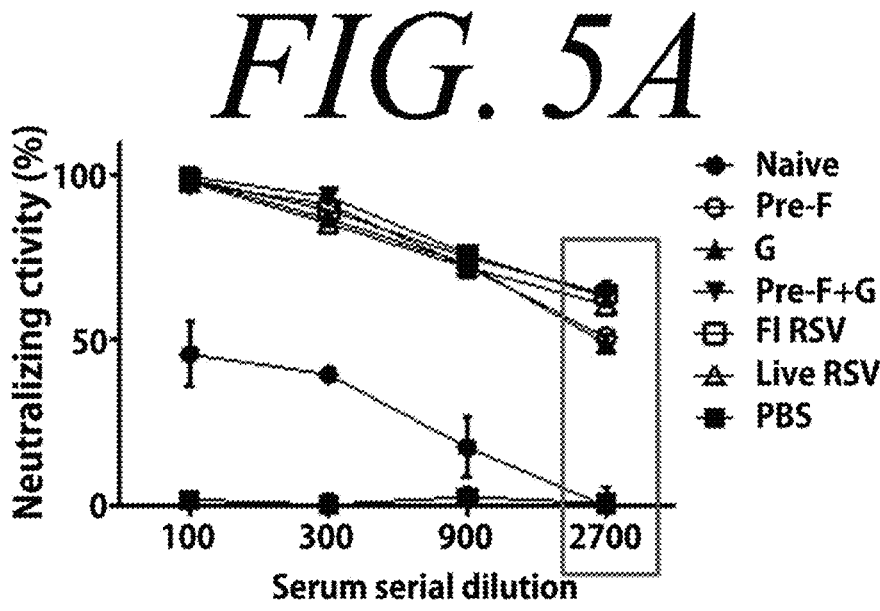
FIG. 5A shows the results confirming the neutralizing activity according to the serial dilution of the groups inoculated with the VLP vaccine prepared according to Example 2-1.
Figure 5B:
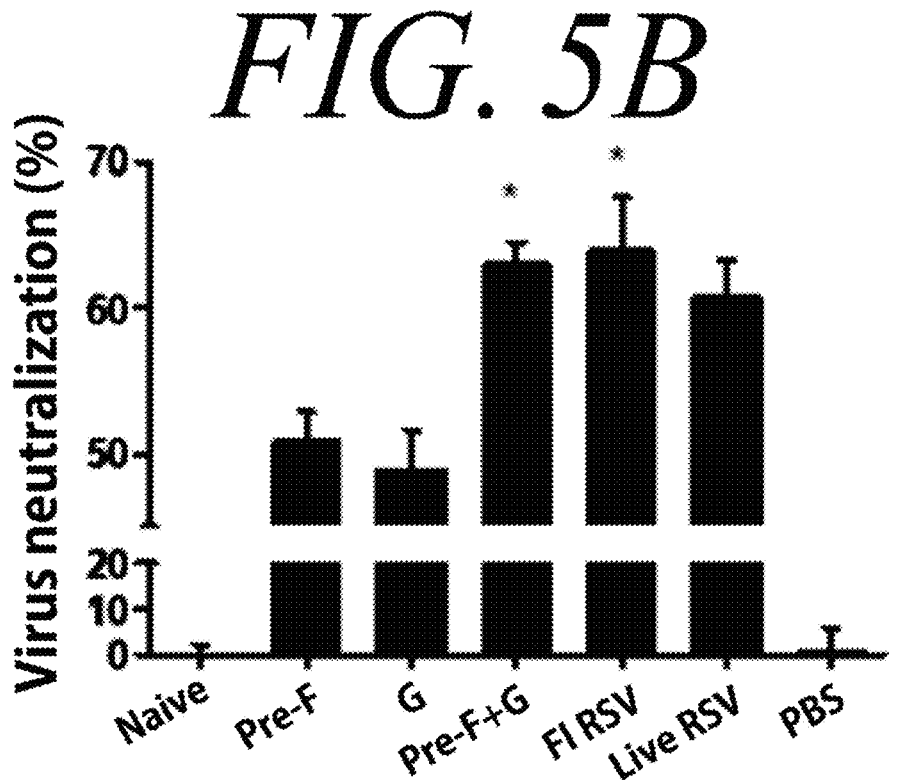
FIG. 5B shows the results confirming the degree of virus neutralization per group at 2700-fold dilution in FIG. 5A.

According to FIGS. 5A and 5B, the groups inoculated with the VLP vaccines according to Example 2-1 maintained higher neutralizing activity compared to the control group (Naive and PBS) even after serial dilution.

Figure 5C:
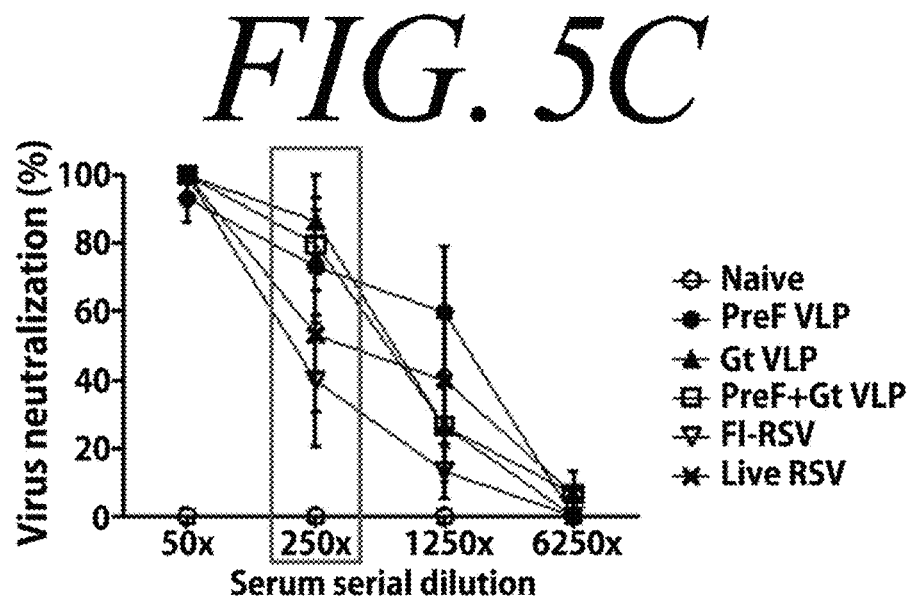
FIG. 5C shows the results confirming the neutralizing activity according to the serial dilution of the groups inoculated with the VLP vaccine prepared according to Example 2-2.
Figure 5D:
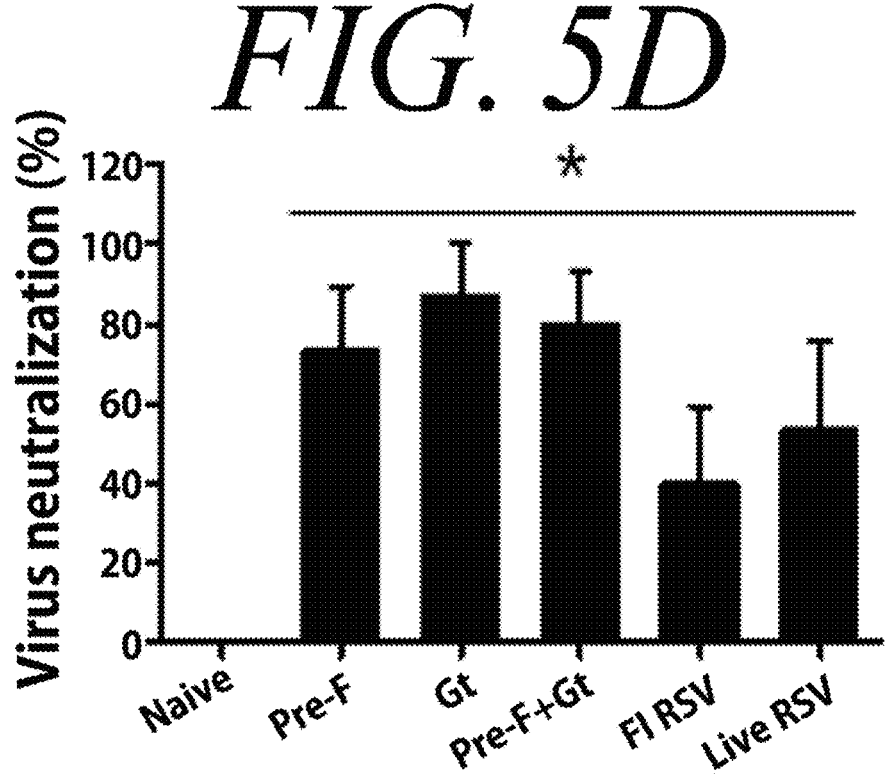
FIG. 5D shows the results confirming the degree of virus neutralization per group at 250-fold dilution in FIG. 5C.

According to FIGS. 5C and 5D, the groups inoculated with the VLP vaccines according to Example 2-1 maintained higher neutralizing activity compared to the control group (Naive) up to the 250-fold dilution.

Figure 6A:
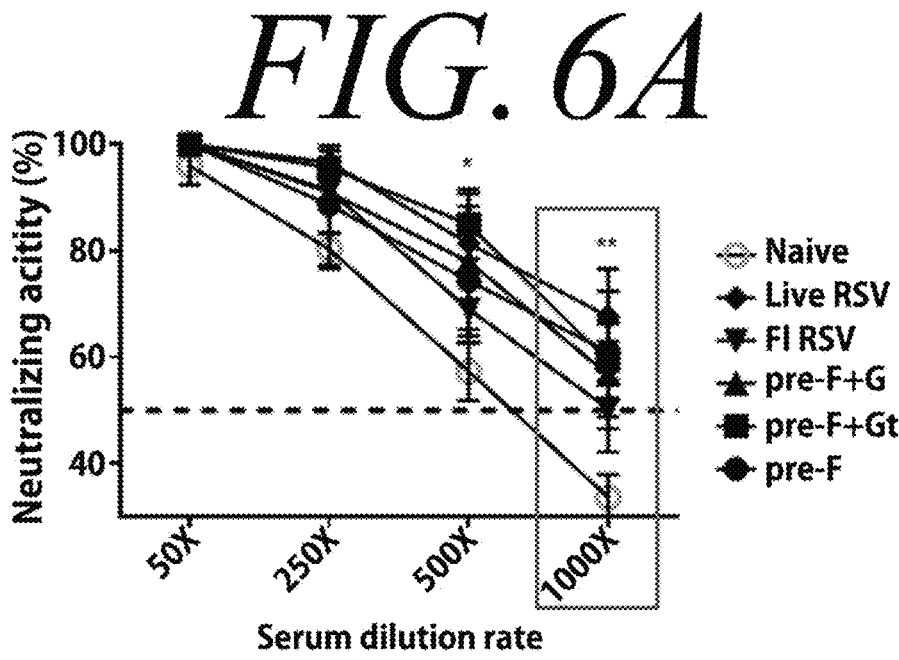
FIG. 6A shows the results confirming the neutralizing activity according to the serial dilution of the groups inoculated with the VLP vaccine prepared according to Example 2-3.
Figure 6B:
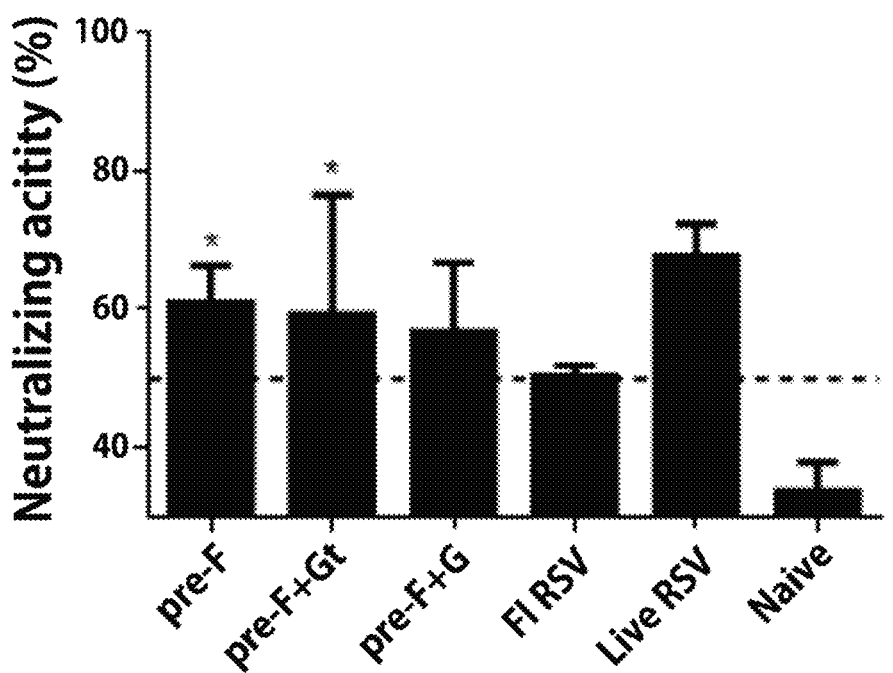
FIG. 6B shows the results confirming the degree of virus neutralization per group at 1000-fold dilution in FIG. 6A.

According to FIGS. 6A and 6B, the groups inoculated with the VLP vaccines according to Example 2-3 maintained higher neutralizing activity compared to the control group (Naive) up to the 1,000-fold dilution.

Example 5: Effect of Influenza M1-Based VLPs on Inhibition of Viral Titers

The lungs of the mice obtained in Example 2 were pulverized in RPMI medium. The pulverized mouse lungs were subjected to centrifugation at 2,000 rpm at 4° C. for 10 minutes to recover the supernatant. Hep-2 cells were dispensed in a 12-well plate and cultured to the confluency of 95% or higher. The pulverized mouse lungs were dispensed into the wells in which the Hep-2 cells were cultured, and incubated at 37° C. for one hour. The pulverized lungs were removed from the wells, and 1 mL of overlay media (a 1:1 mixture of 1% noble agar and DMEM media) was dispensed into each well and incubated at 37° C. for 3 to 4 days. After removing the overlay media, a fixative (acetone+methanol) was added to the Hep-2 cells and incubated at room temperature for 20 minutes to fix the cells. The fixed cells were treated with a primary antibody against RSV-preF (anti-RSV Fusion monoclonal Ab (1:2,000)) and incubated at 37° C. for one hour. The cells were washed with PBS, treated with a secondary antibody (IgG-HRP conjugated Ab (1:3,000)), and incubated at 37° C. for one hour. After washing the cells with PBS, the cells were treated with a DAB colorant and then incubated at room temperature for 20 to 30 minutes.

In addition, a control group was prepared in the same manner by infecting the uninoculated uninfected group (Naive), non-vaccinated infected group (Naive+challenge), FI-RSV (Formalin inactivate RSV) vaccinated group, and Live RSV-infected group with RSV A2. FI-RSV was included as an inactive vaccine and was included as a standard for an inferior vaccine with a high inflammatory response, and Live RSV, as a cured mouse after RSV infection, was included as a standard for an excellent vaccine with an excellent immune response while having a low inflammatory response. As the prepared vaccine has a lower viral titer and inflammatory response than FI-RSV, and shows an effect comparable to that of the LIVE RSV experimental group, the prepared vaccine can be evaluated as having superior performance as a vaccine.

Figure 7A:
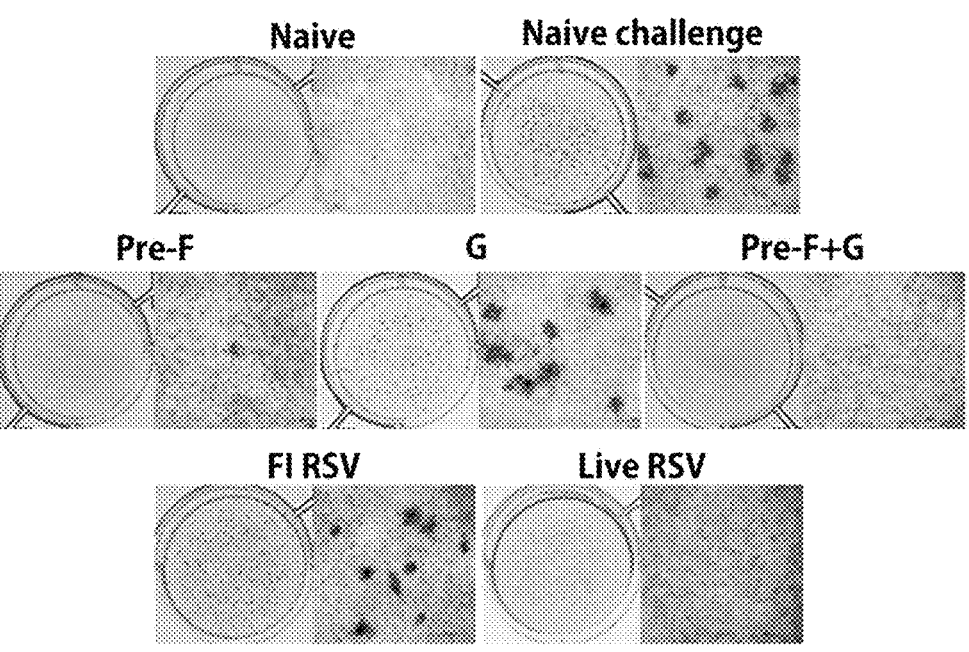
FIG. 7A shows the images illustrating lung tissue obtained from the mice infected with RSV A2 after immunization with the VLP having influenza M1 as a core protein according to Example 2-1 and pulverized in RPMI medium.
Figure 7B:
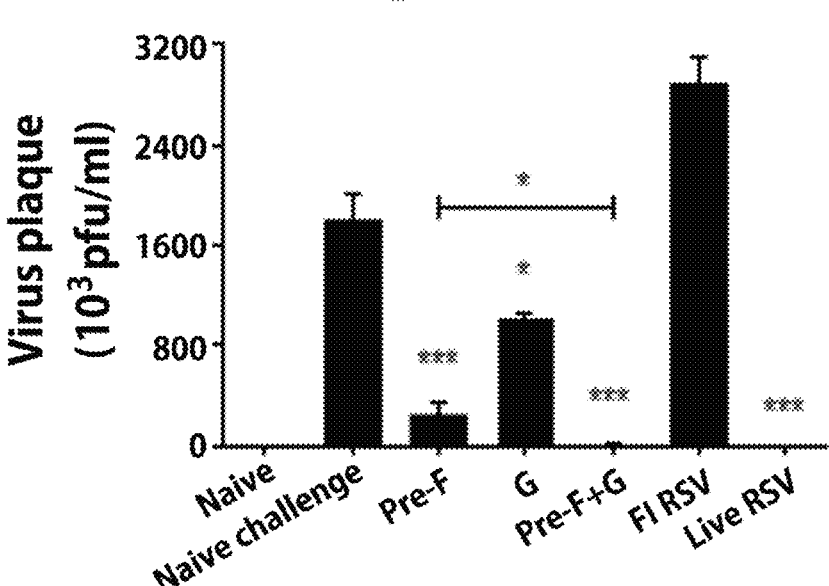
FIG. 7B shows the results of quantification of the virus titers of lung tissue of the mice infected with RSV A2 by Plaque assay after immunization with the VLP having influenza M1 as a core protein according to Example 2-1.

According to FIGS. 7A and 7B, the group inoculated with RSV-PreF M1 VLP and the group inoculated with RSV-PreF+G M1 VLP showed a significant decrease of the viral titer of the lungs compared to the control group (non-vaccinated infected group and FI RSV), and it was also confirmed that the virus plaque formation was low enough showing almost no difference from the Live RSV-infected group. It appears that VLPs displaying both RSV-preF and RSV-G have caused a synergistic effect from the aspect of immune induction.

Figure 8A:
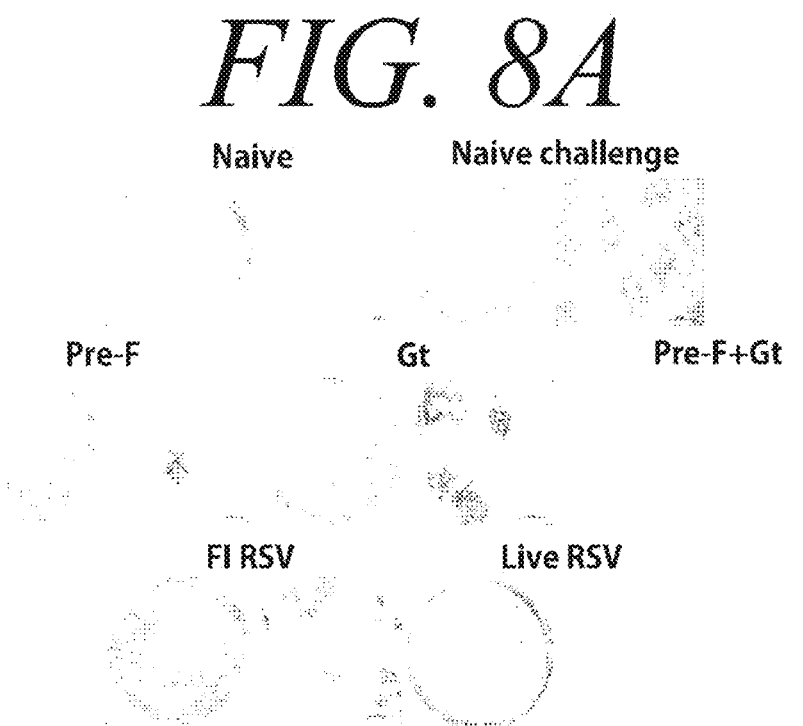
FIG. 8A shows the images illustrating lung tissue obtained from the mice infected with RSV A2 after immunization with the VLP having influenza M1 as a core protein according to Example 2-2 and pulverized in RPMI medium.
Figure 8B:
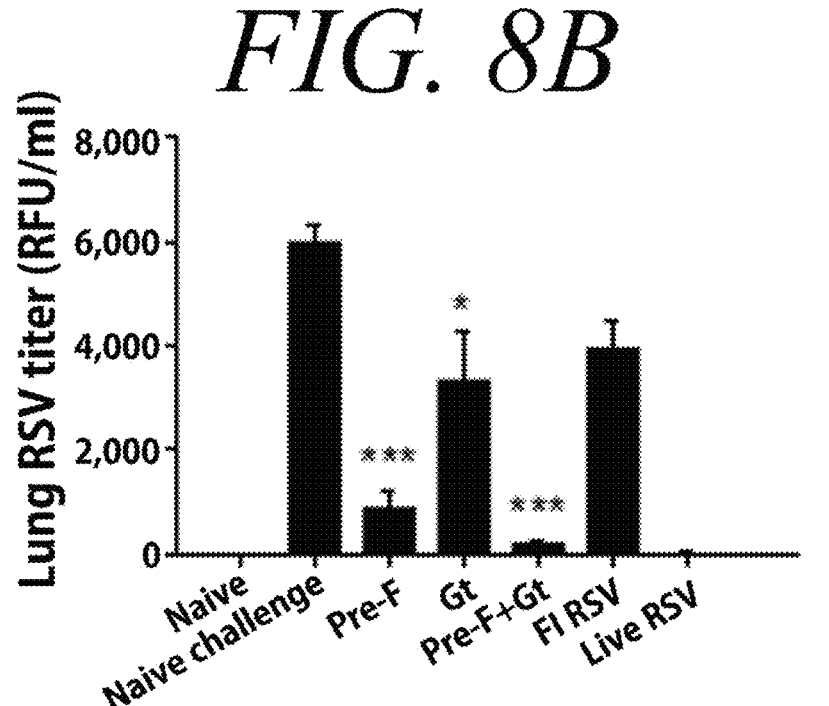
FIG. 8B shows the results of quantification of the virus titers of lung tissue of the mice infected with RSV A2 by Plaque assay after immunization with the VLP having influenza M1 as a core protein according to Example 2-2.

According to FIGS. 8A and 8B, the group inoculated with RSV-preF+RSV-Gt+M1 VLP showed a significantly reduced viral titer of the lungs compared to the group inoculated with RSV-preF+M1 VLP and the group inoculated with RSV-Gt+M1 VLP inoculation group, and it was also confirmed that the virus plaque formation was also low enough showing almost no difference from the Live RSV-infected group. It appears that VLPs displaying both RSV-preF and RSV-Gt have caused a synergistic effect from the aspect of immune induction. The VLPs in which two kinds of antigenic proteins are displayed do not necessarily have a higher effect than the VLPs in which one antigen is displayed, and in some cases, one type of antigen may not work or the effect may be even lowered. Therefore, it appears to be difficult to predict the improvement of the immune effect of VLPs displaying both RSV-preF and RSV-Gt without experimental confirmation.

Figure 9A:
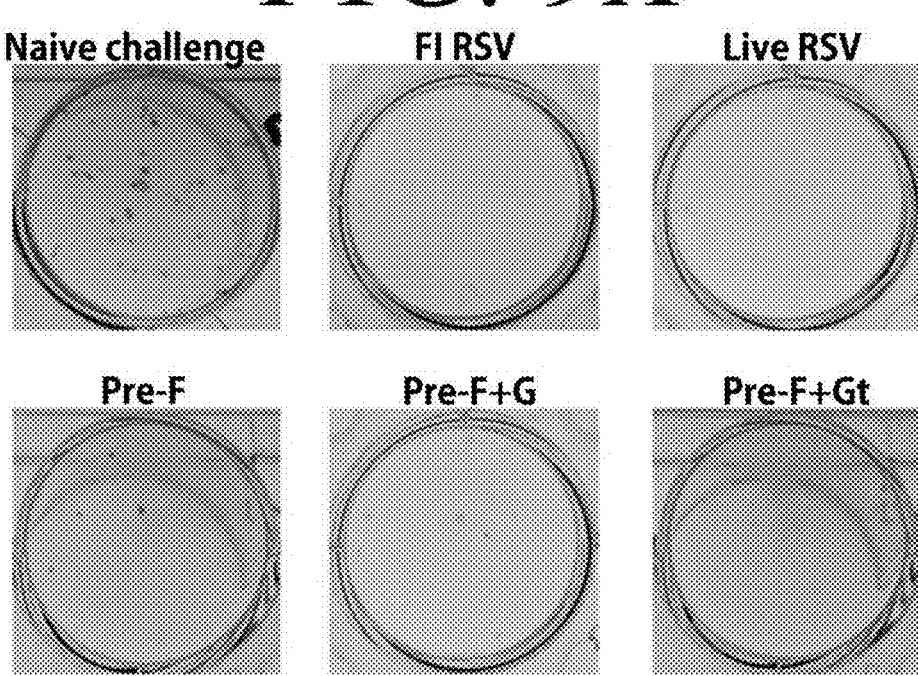
FIG. 9A shows the images illustrating lung tissue obtained from mice infected with RSV rA2 cell line 19F after immunization with the VLP having influenza M1 as a core protein according to Example 2-3 and pulverized in RPMI medium.
Figure 9B:
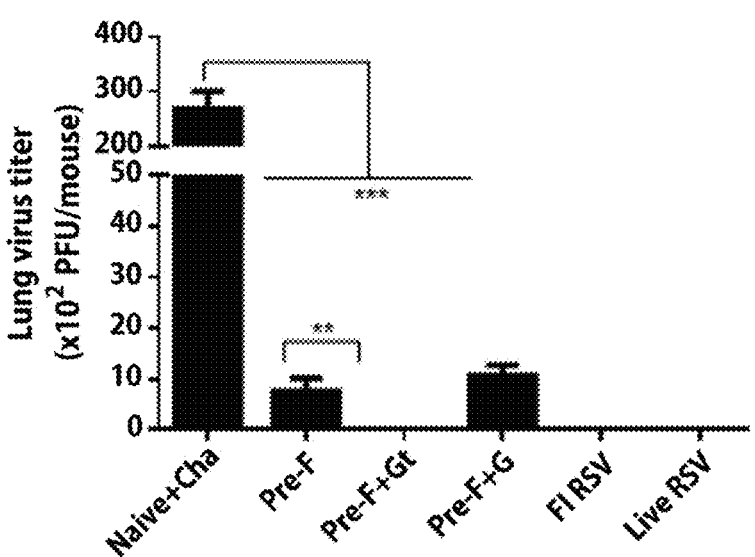
FIG. 9B shows the results of quantification of the virus titers of lung tissue of mice infected with RSV rA2 cell line 19F by Plaque assay after immunization with the VLP having influenza M1 as a core protein according to Example 2-3.

Virus titers were confirmed in the same manner as above, except that RSV rA2 cell line 19F was used as the RSV virus. According to FIGS. 9A and 9B, it was confirmed that the group inoculated with RSV-preF+M1 VLP, the group inoculated with RSV-preF+RSV-preF+Gt+M1 VLP, and the group inoculated with RSV-preF+RSV-preF+G+M1 VLP showed a significant decrease in the viral titer of the lungs compared to the unvaccinated infected group, and also that the virus plaque formation was low enough showing almost no difference from the Live RSV-infected group.

Example 6: Comparison of Effects with VLPs Including RSV-M as Core Protein

Figure 10A:
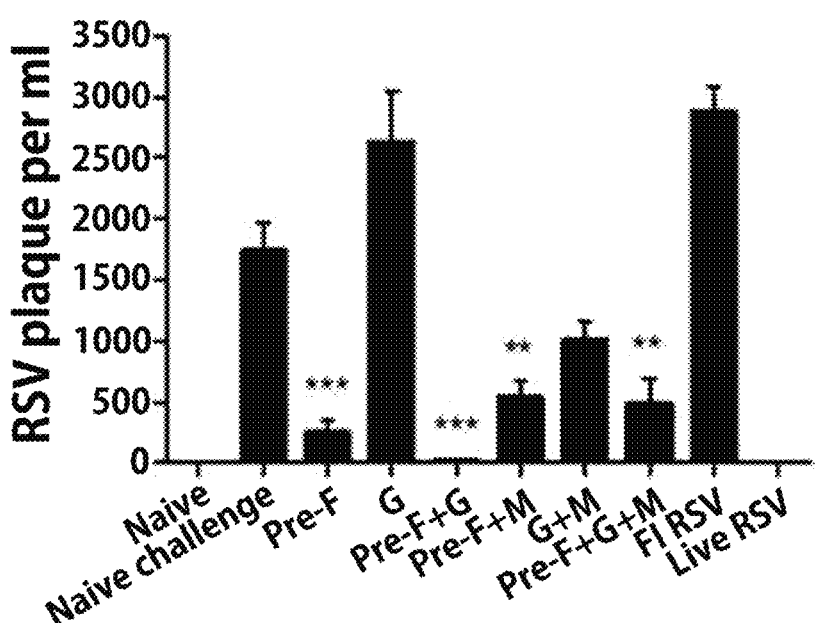
FIG. 10A shows the comparison results of the virus titers of lung tissue of the mice immunized with a VLP including influenza M1 as a core protein and the mice immunized with a VLP including RSV-M as a core protein, after infecting these mice with RSV A2. PreF, G, and preF+G are experimental groups immunized with VLPs including M1 as a core protein, and preF+M, G+M, and preF+G+M are experimental groups immunized with VLPs including RSV-M as a core protein.
Figure 10B:
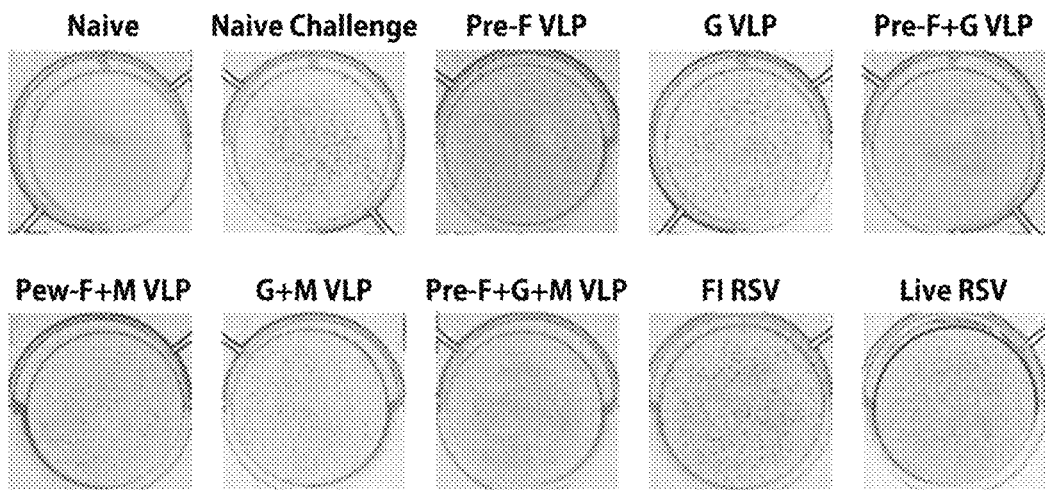
FIG. 10B shows the images illustrating the lung tissue obtained from the mice immunized with a VLP including influenza M1 as a core protein and the mice immunized with a VLP including RSV-M as a core protein, after infecting these mice with RSV A2 followed by pulverization in RPMI medium.

Mice immunized with RSV-M or M1 as a core protein were infected with RSV A2 virus, and the virus titer was confirmed in the same manner as in Example 2. According to FIG. 10, VLPs having RSV-M as the core protein and the VLPs having influenza M1 as the core protein, although both having the same antigen protein on the surface thereof, showed a difference in the virus titer due to the difference in the core protein. In the VLPs having RSV-G as a surface protein, the VLPs having influenza M1 as a core showed a higher viral titer compared to the VLPs having RSV-M as a core. However, in the VLPs whose surface protein is RSV-preF or RSV-preF/RSV-G, the VLPs having influenza M1 as a core showed a lower viral titer compared to the VLPs having RSV-M as a core. This suggests that differences in effect may occur depending on the combination of the core protein and the surface protein, and as for the RSV-preF surface protein, the immune effect of the chimeric VLPs combined with influenza M1 was superior to the VLPs combined with RSV-M.

Example 7: Experiment on Lung Inflammation

A 10% buffered formalin solution was injected into the lungs of the mice obtained in Example 2. After the dehydration process, the lungs were hardened with paraffin to prepare paraffin blocks. The paraffin blocks were subjected to micro-sectioning for tissue section and placed them on top of glass slides. The slides on which the tissue sections were mounted were washed 3 times with 100% xylene to remove paraffin. The slides were immersed in 100%-90%-80%-50%

EtOH twice for 10 minutes. The prepared specimens were stained with Hematoxylin and Eosin (H&E) or Periodic Acid Schiff (PAS).

Figure 11A:
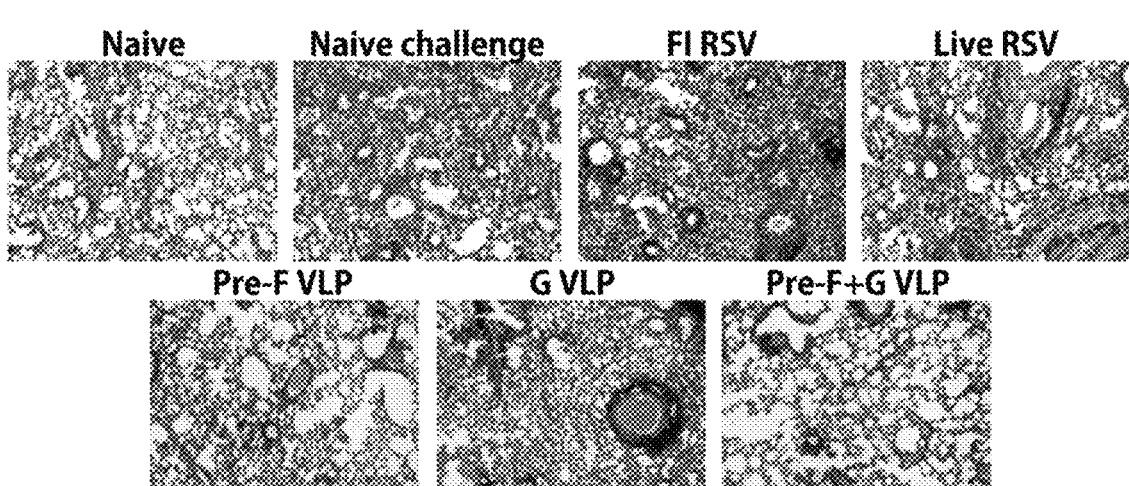
FIG. 11A shows the results of leukocyte concentrations, observed after H&E staining, in the lung tissue of the mice infected with RSV A2 after immunization with the VLP according to Example 2-1 (100× magnification under a microscope).
Figure 11B:
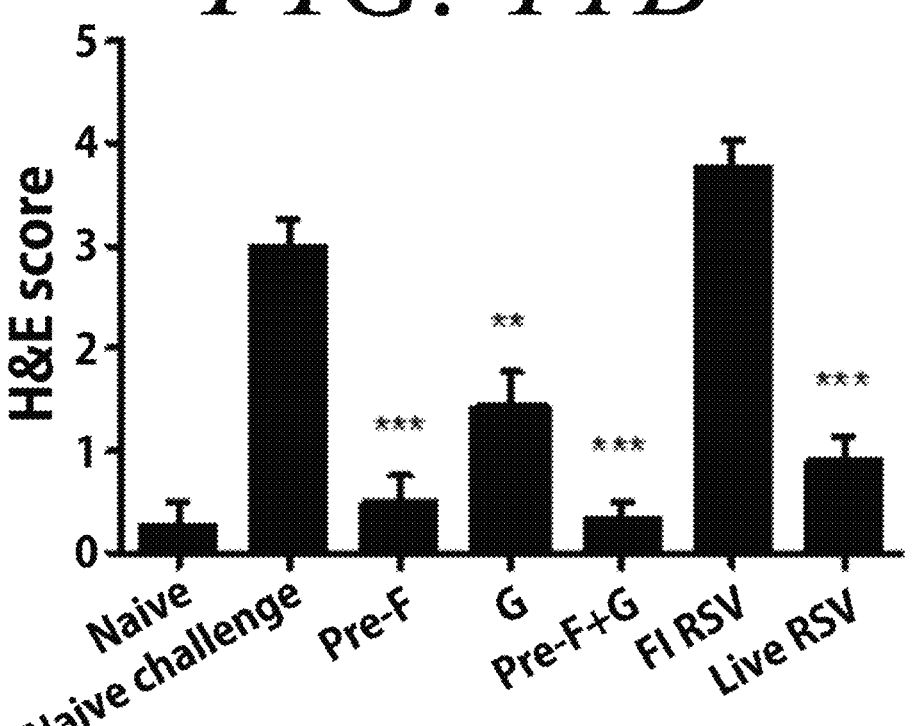
FIG. 11B shows the scoring of the results of the tissue section staining images of FIG. 11A, in which a score of 0 indicates no symptoms and a score of 5 indicates severe symptoms.
Figure 11C:
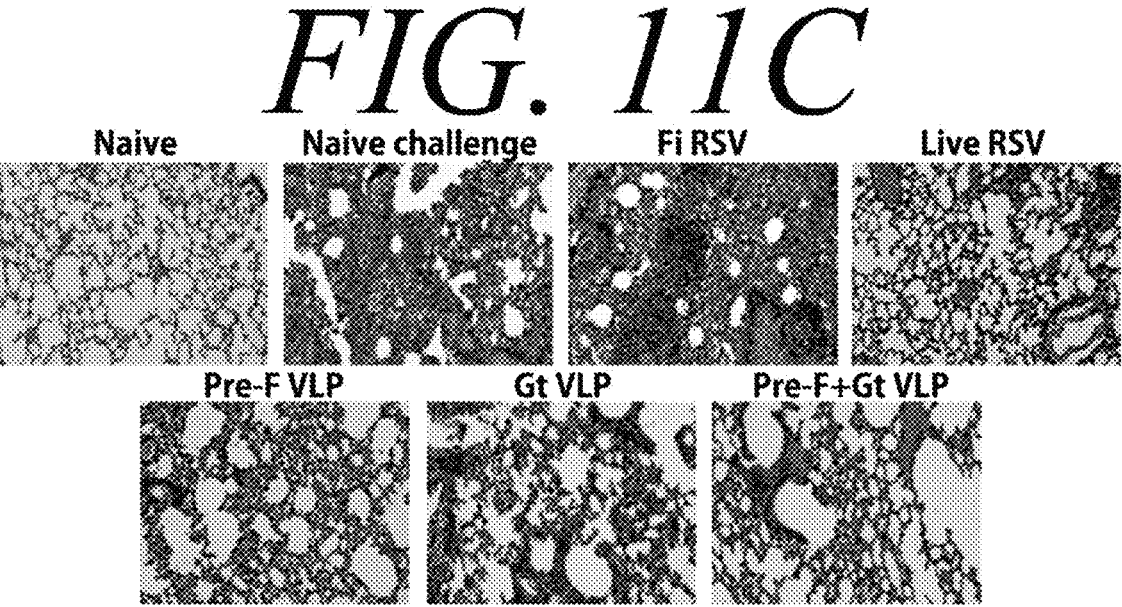
FIG. 11C shows the results of leukocyte concentrations, observed after H&E staining, in the lung tissue of the mice infected with RSV A2 after immunization with the VLP according to Example 2-2 (100× magnification under a microscope).
Figure 11D:
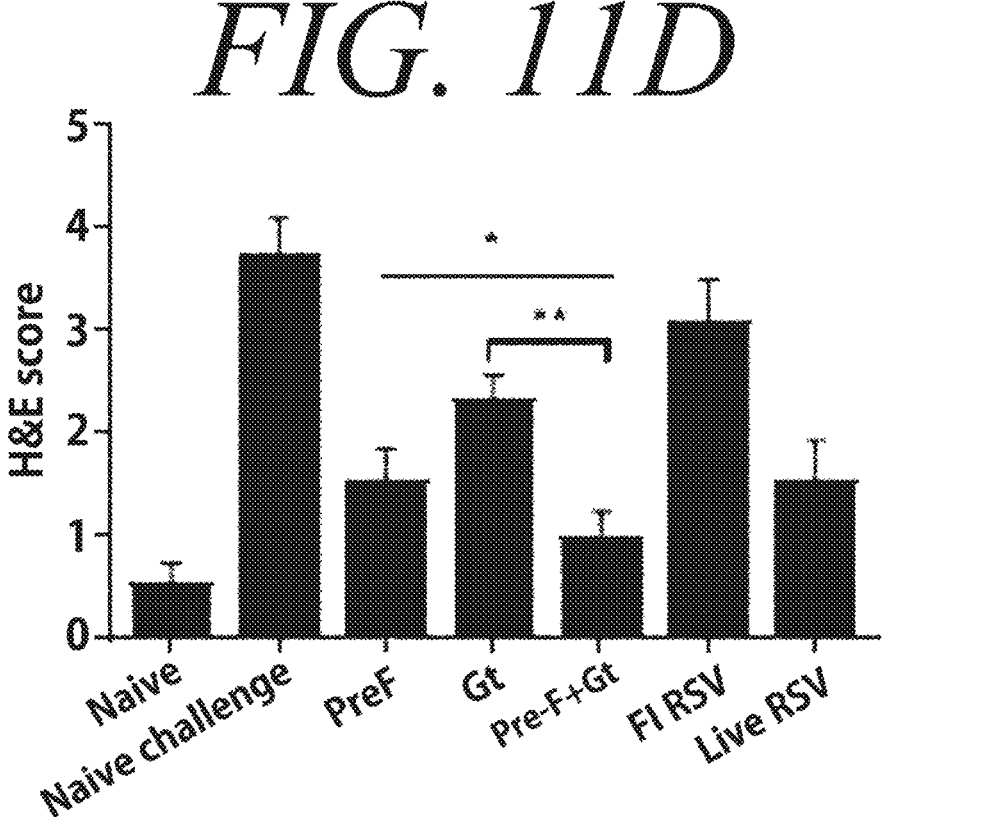
FIG. 11D shows the scoring of the results of the tissue section staining images of FIG. 11C, in which a score of 0 indicates no symptoms and a score of 5 indicates severe symptoms.

FIG. 11A shows the results of H&E staining of Example 2-1, FIG. 11B shows the results of H&E scores of Example 2-1, FIG. 11C shows the results of H&E staining of Example 2-2, and FIG. 11D shows the results of H&E scores of Example 2-2. According to the H&E staining results of FIGS. 11A and 11C, while the empty alveolar structure in the unvaccinated and uninfected group (Naive) was shown to be large and clear, in the naive challenge group, the alveolar size was significantly reduced due to the concentration of leukocytes. The group inoculated with RSV-preF+RSV-G+M1 VLP and the group inoculated with RSV-preF+RSV-Gt+M1 VLP showed structures similar to that of the Naive or Live RSV-infected group despite RSV A2 infection. Therefore, it was confirmed that the group inoculated with RSV-preF+RSV-G+M1 VLP of Example 2-1 and the group inoculated with RSV-preF+RSV-Gt+M1 VLP of Example 2-2 showed the lowest concentration of leukocytes and the lowest induction of inflammation.

FIGS. 11B and 11D show the staining results of FIGS. 11A and 11C expressed as scores, respectively, in which a score of 0 indicates no symptoms and a score of 5 indicates severe symptoms. It was confirmed that the mice immunized with the VLPs expressing preF and G in Example 2-1 and the mice immunized with the VLPs expressing preF and Gt in Example 2-2 had a lower concentration of leukocytes in the lungs and less inflammatory side effects compared to the Live RSV experimental group upon RSV infection.

Figure 12A:
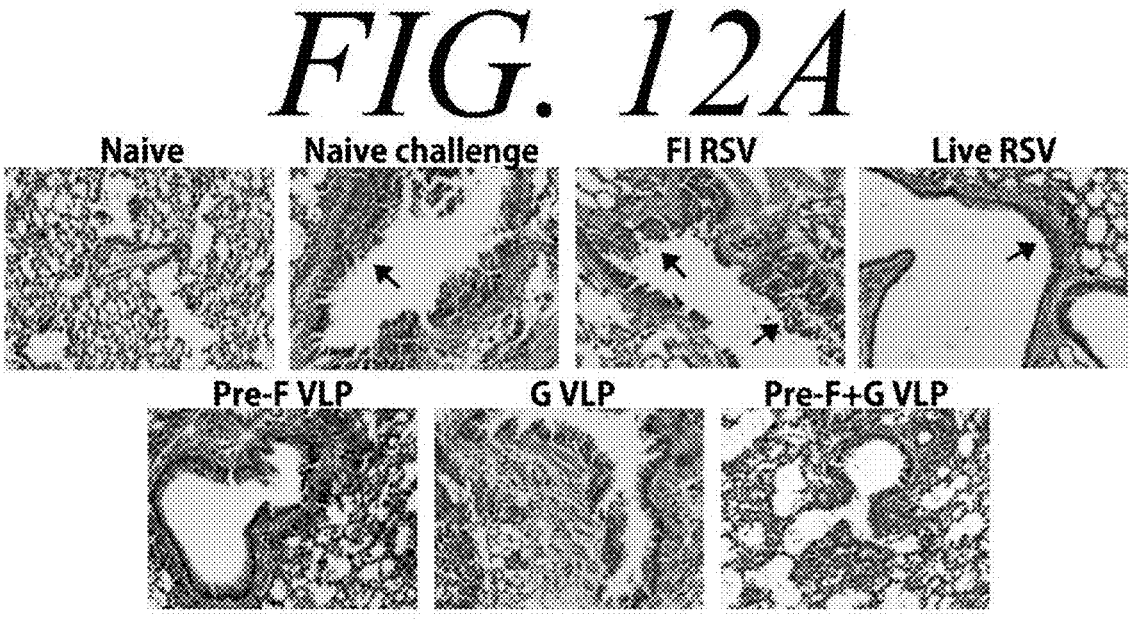
FIG. 12A shows the results confirming the degree of inflammation, after staining with Periodic Acid Schiff (PAS), in the lung tissue of the mice infected with RSV A2 after immunization with the VLP according to Example 2-1. The PAS staining stains the mucin glycoprotein secreted by inflammation from the inner surface of the alveoli, and the dark purple section indicated by the black arrow is mucin.
Figure 12B:
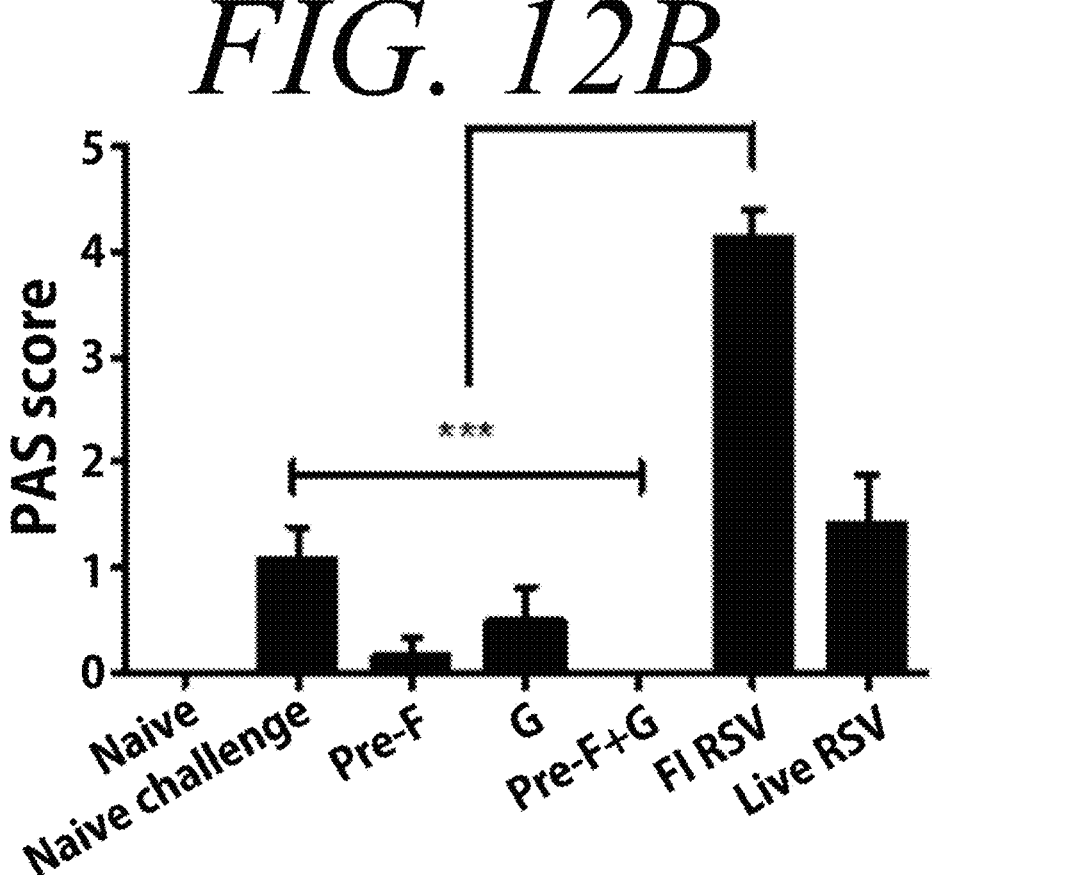
FIG. 12B shows the scoring of the results of the tissue section staining images of FIG. 12A, in which a score of 0 indicates no symptoms and a score of 5 indicates severe symptoms.
Figure 12C:
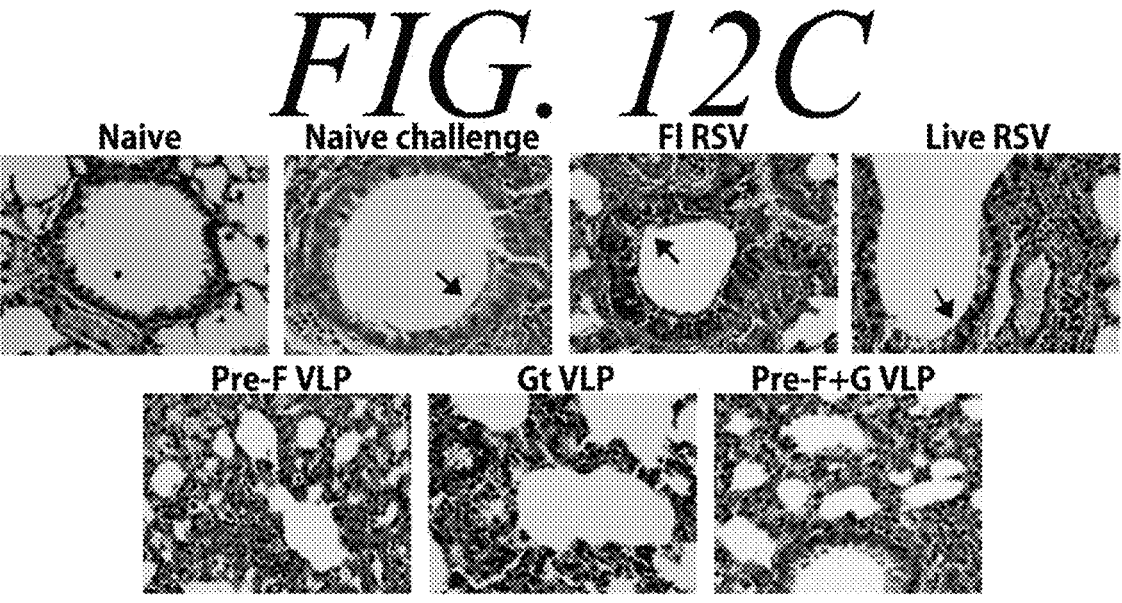
FIG. 12C shows the results confirming the degree of inflammation, after staining with Periodic Acid Schiff (PAS), in the lung tissue of the mice infected with RSV A2 after immunization with the VLP according to Example 2-2. The PAS staining stains the mucin glycoprotein secreted by inflammation from the inner surface of the alveoli, and the dark purple section indicated by the black arrow is mucin.
Figure 12D:
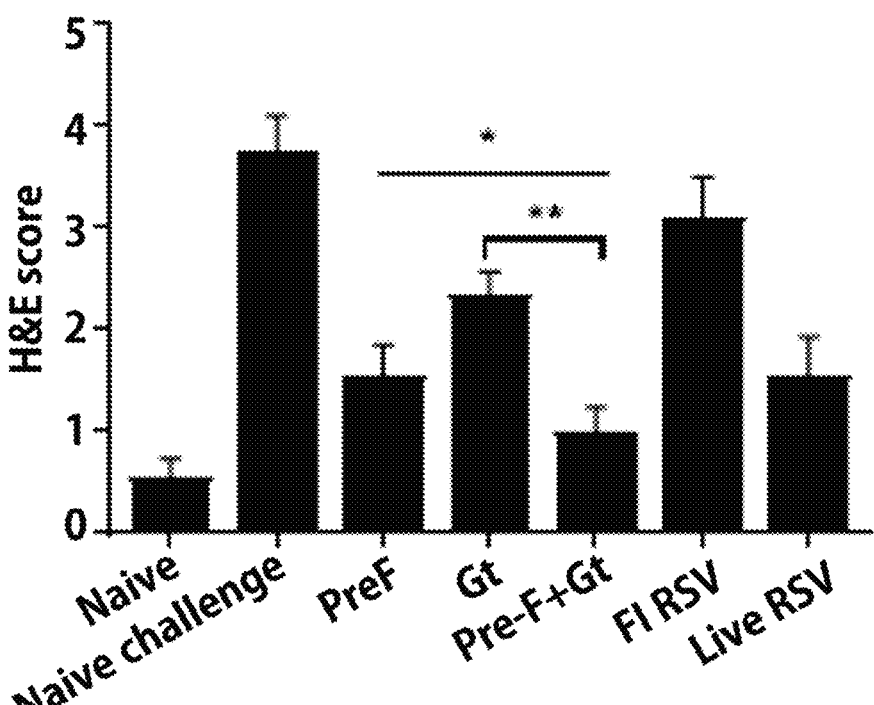
FIG. 12D shows the scoring of the results of the tissue section staining images of FIG. 12C, in which a score of 0 indicates no symptoms and a score of 5 indicates severe symptoms.

FIG. 12A shows the PAS staining results of Example 2-1, FIG. 12B shows the PAS scores of Example 2-1, FIG. 12C shows the PAS staining results of Example 2-2, and FIG. 12D shows the PAS scores of Example 2-2. According to the PAS staining results of FIGS. 12A and 12C, the unvaccinated and uninfected group (Naive) did not have abnormal mucin secretion, and thus dark purple PAS staining did not appear. However, the Naive Challenge group had active mucin secretion and thus dark purple PAS staining was observed. The group inoculated with RSV-preF+M1 VLP and the group inoculated with RSV-preF+RSV-G+M1 VLP in Example 2-1, and the group inoculated with RSV-preF+RSV-Gt+M1 VLP and the group inoculated with RSV-preF+M1 VLP in Example 2-2 showed almost no expression of mucin protein compared to other experimental groups and the control group (see arrows in FIGS. 12A and 12C), thus confirming that the inflammatory response was significantly alleviated.

FIGS. 12B and 12D each show the scoring of the results of the tissue section staining images of FIGS. 12A and 12C, in which a score of 0 indicates no symptoms and a score of 5 indicates severe symptoms. It was confirmed that, upon RSV infection, the mice immunized with the VLPs that express preF and G in Example 2-1 and the mice immunized with the VLPs that express preF and Gt in Example 2-2 showed a lower leukocyte concentration and mucin expression and lower inflammatory side effects in the lungs compared to the Live RSV experimental group.

Figure 13A:
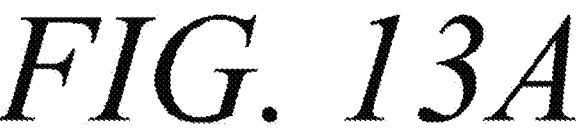
FIG. 13A shows the results of leukocyte concentrations, observed after H&E staining, in the lung tissue of the mice infected with RSV rA2 cell line 19F after immunization with the VLP according to Example 2-3 (100× magnification under a microscope).
Figure 13A:
Figure 13A:
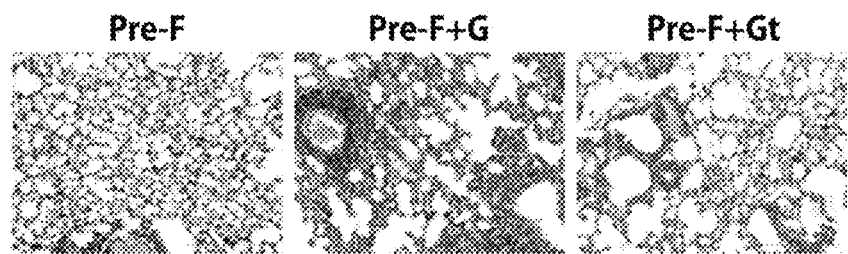
Figure 13B:
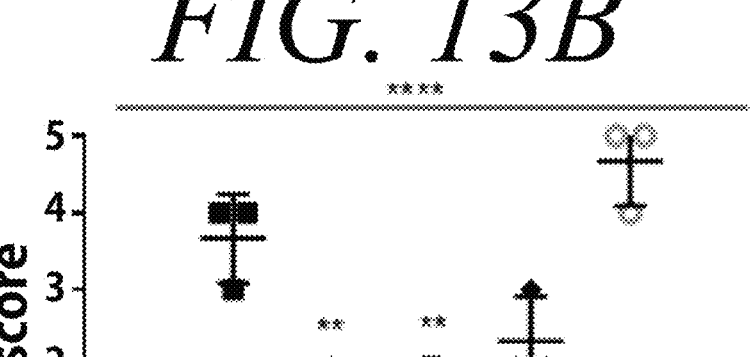
FIG. 13B shows the scoring of the results of the tissue section staining images of FIG. 13A, in which a score of 0 indicates no symptoms and a score of 5 indicates severe symptoms.
Figure 13B:
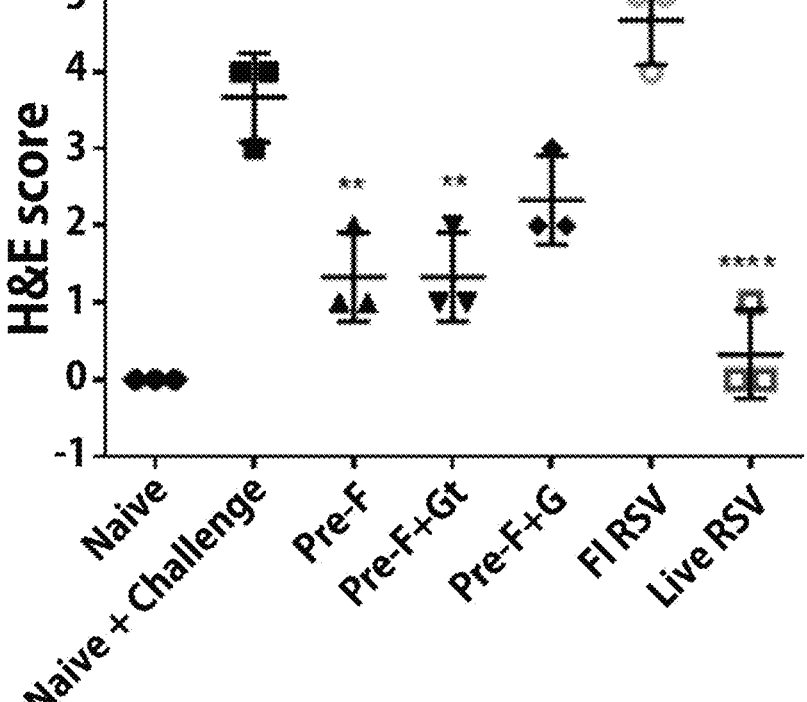

FIG. 13A shows the H&E staining results of Example 2-3 and FIG. 13B shows the H&E scores of Example 2-3. According to the H&E staining result of FIG. 13A, the empty alveolar structure was large and clear in the unvaccinated and uninfected group (Naive); however, in the Naive Challenge group, the alveolar size was significantly reduced due to the concentration of leukocytes. The group inoculated with RSV-preF+M1 VLP, the group inoculated with RSV-preF+RSV-G+M1 VLP, and the group inoculated with RSVpreF+RSV-Gt+M1 VLP showed structures similar to that of the Naive or Live RSV-infected group despite the RSV rA2 cell line 19F infection.

FIG. 13B shows the scoring of each of the results of the tissue section staining images of FIG. 13A the tissue section staining photograph of FIG. 13A, in which a score of 0 indicates no symptoms and a score of 5 indicates severe symptoms. In Example 2-3, it was confirmed that upon RSV rA2 cell line 19F infection, the mice immunized with VLPs expressing preF and the mice immunized with VLPs expressing preF and G, or preF and Gt had a lower concentration of leukocytes and lower inflammatory side effects in the lungs compared to the Live RSV experimental group.

Figure 14A:
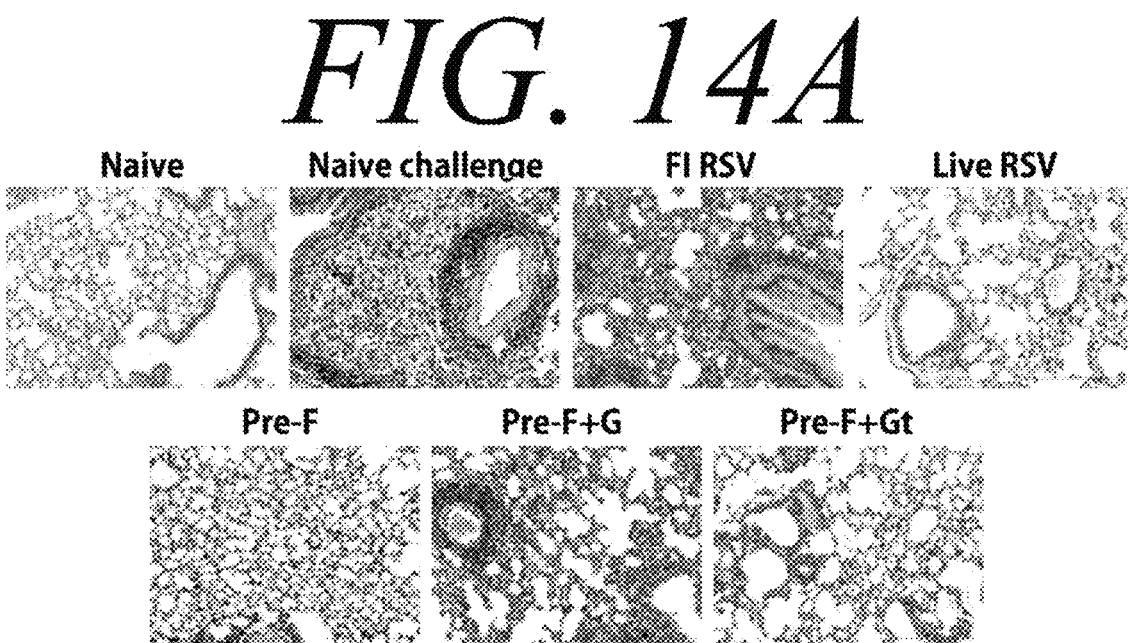
FIG. 14A shows the results confirming the degree of inflammation, after staining with Periodic Acid Schiff (PAS), in the lung tissue of the mice infected with RSV rA2 cell line 19F after immunization with the VLP according to Example 2-3. The PAS staining stains the mucin glycoprotein secreted by inflammation from the inner surface of the alveoli, and the dark purple section indicated by the black arrow is mucin.
Figure 14B:
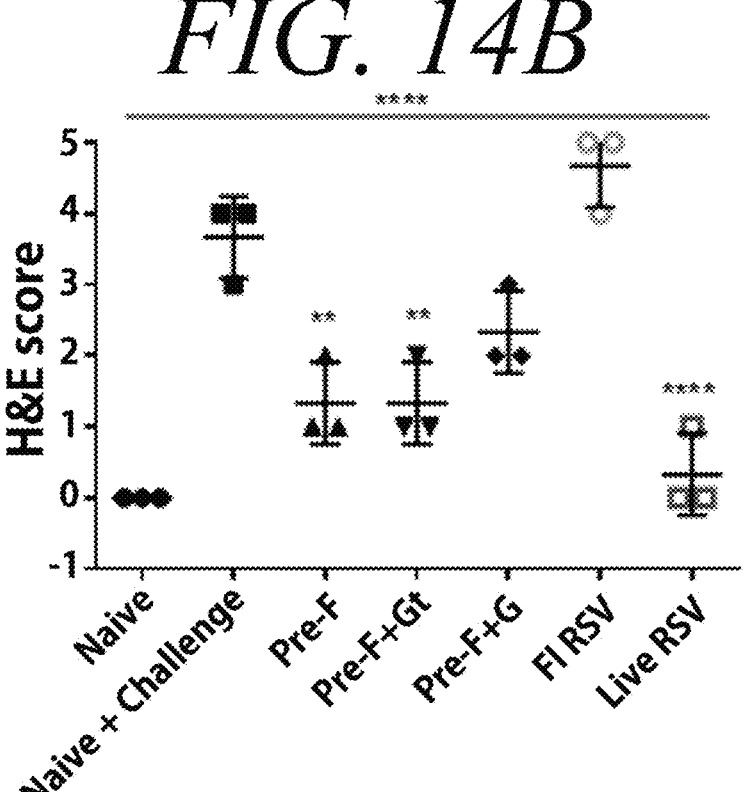
FIG. 14B shows the scoring of the results of the tissue section staining images of FIG. 14A, in which a score of 0 indicates no symptoms and a score of 5 indicates severe symptoms.

FIG. 14A shows the PAS staining results of Example 2-3 and FIG. 14B shows the PAS scores of Example 2-3. According to the PAS staining results of FIG. 14A, the unvaccinated and uninfected group (Naive) did not have abnormal mucin secretion, and thus dark purple PAS staining did not appear. However, the Naive Challenge group had active mucin secretion and thus dark purple PAS staining was observed. The group inoculated with RSV-preF+M1 VLP the group inoculated with RSV-preF+RSV-G+M1 VLP, and the group inoculated with RSV-preF+RSV-Gt+M1 VLP in Example 2-3 showed almost no expression of mucin protein compared to other experimental groups and the control group (see arrows in FIGS. 14A), thus confirming that the inflammatory response was significantly alleviated.

FIG. 14B shows the scoring of the results of the tissue section staining images of FIG. 14A, in which a score of 0 indicates no symptoms and a score of 5 indicates severe symptoms. In Example 2-3, it was confirmed that upon RSV rA2 cell line 19F infection, the mice immunized with VLPs expressing preF and the mice immunized with VLPs expressing preF and G, or preF and Gt had a lower concentration of leukocytes and lower inflammatory side effects in the lungs compared to the Live RSV experimental group.

The mice inoculated with VLPs having RSV-M as a core protein were infected with RSV A2, and the inhibitory effect on lung inflammation was confirmed in the same manner as above.

Figure 15A:
FIG. 15A shows the results of leukocyte concentrations, observed after H&E staining, in the lung tissue of the mice infected with RSV A2 after immunization with a VLP having a different core protein (RSV-M or influenza M1).
Figure 15A:
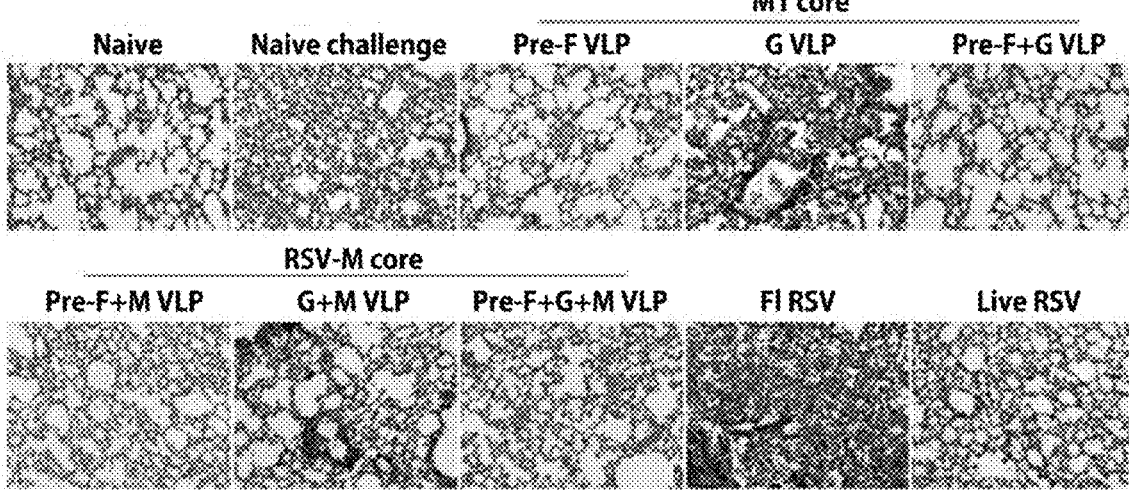

According to the H&E staining results of FIG. 15A, it was confirmed that there is a difference in the degree of inflammatory response according to the difference in the core protein even if the antigen proteins displayed on the VLP surface are the same. Among the M1-based VLPs, the VLPs including (preF+G) showed a low inflammatory response to such an extent that there was no morphological difference from Naive or Live RSV. However, among the RSV-M-based VLPs, the preF+G+M VLPs, although having the surface-displayed proteins as pre-F+G+M1 VLPs, showed higher levels of leukocyte concentration and inflammatory responses.

Figure 15B:
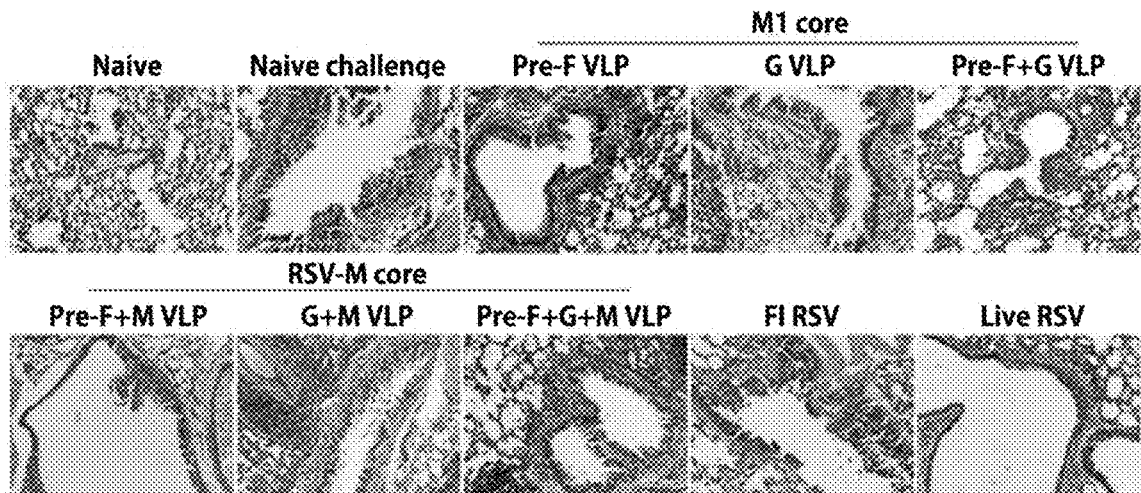
FIG. 15B shows the results confirming the degree of inflammation, after staining with Periodic Acid Schiff (PAS), in the lung tissue of the mice infected with RSV A2 after immunization with a VLP having a different core protein (RSV-M or influenza M1).

According to the PAS staining results of FIG. 15B, it was confirmed that there is a difference in mucin secretion according to the difference in the core protein even if the antigen proteins displayed on the VLP surface are the same. While among the M1-based VLPs, VLPs including (preF+G) did not show PAS staining similarly to Naive and Live RSV groups, among the RSV-M-based VLPs, the (preF+G) showed stronger PAS staining although the surface-displayed proteins are the same.

Figure 16A:
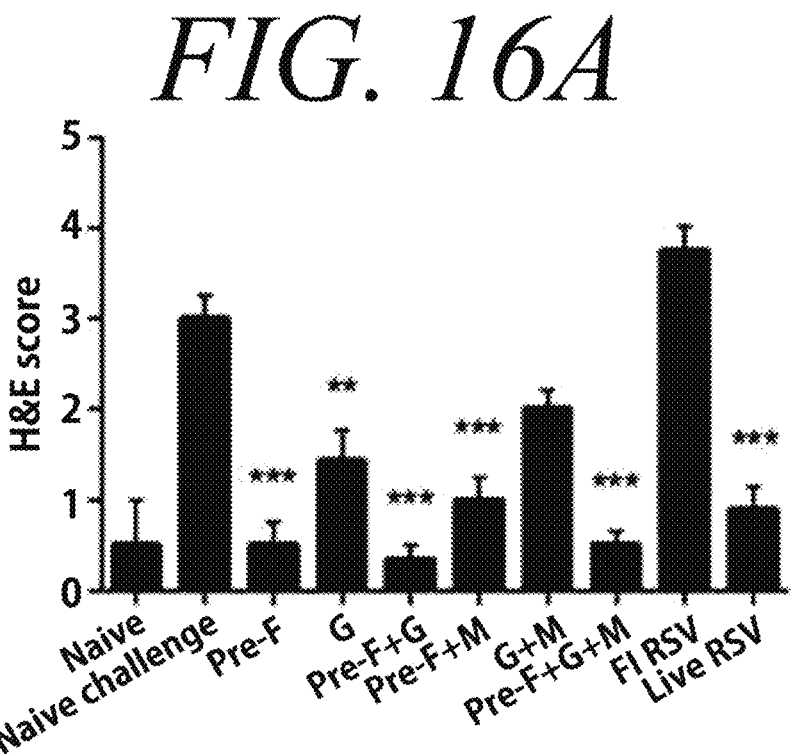
FIG. 16A shows the scoring of the results of the tissue section staining images of FIG. 15A, in which a score of 0 indicates no symptoms and a score of 5 indicates severe symptoms.
Figure 16B:
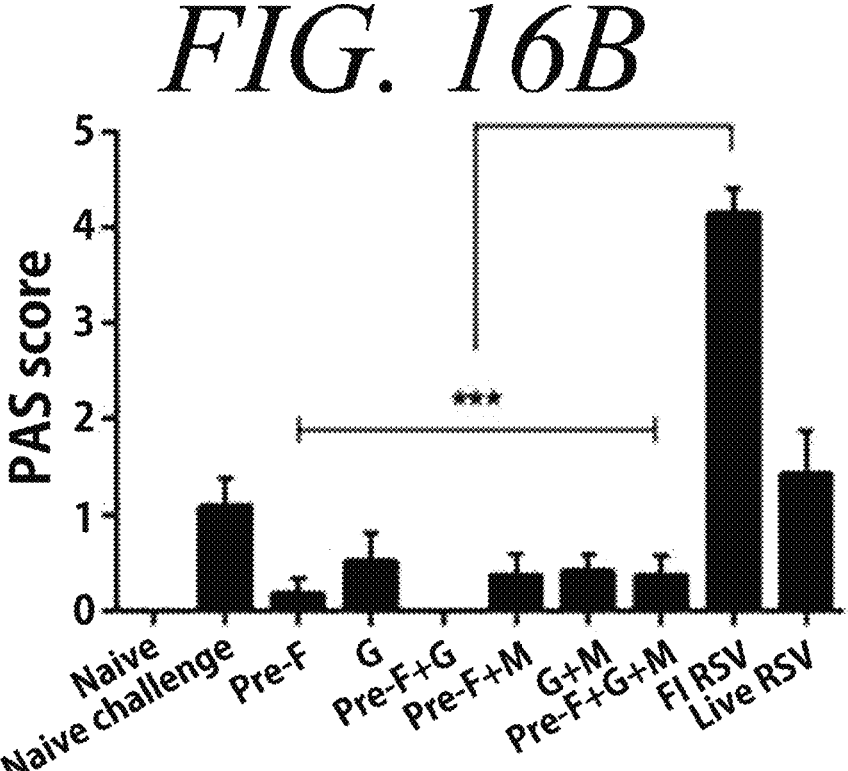
FIG. 16B shows the scoring of the results of the tissue section staining images of FIG. 15B, in which a score of 0 indicates no symptoms and a score of 5 indicates severe symptoms.

FIGS. 16A and 16B each show the scoring of the results of the tissue section staining images of FIGS. 15A and 15B, in which a score of 0 indicates no symptoms and a score of 5 indicates severe symptoms. It was confirmed that the mice immunized with influenza M1 as a core VLP, upon RSV infection, had lower leukocyte concentration and mucin expression and lower inflammatory side effects in the lungs compared to the mice immunized with VLPs having RSV-M as the core protein.

Summarizing the above experimental results, it was confirmed that the VLPs, in which RSV-preF+RSV-G or RSV-preF+RSV-Gt are displayed from the aspect of surface antigen proteins, have an excellent immune effect against RSV and low side effects, such as inflammatory response of the lungs, compared to that of VLPs, in which only one of preF, G, and Gt of RSV is displayed.

Further, from the aspect of the core proteins being combined with RSV-preF or RSV-preF+RSV-G, it was confirmed that the VLPs having influenza M1 as the core were superior to the VLPs including RSV-M as the core in terms of immune effect and reduction of pulmonary inflammatory responses.

Example 8: Confirmation of Eosinophilia

The lungs of the mice obtained in Example 2-1 were pulverized and centrifuged at 2,000 rpm for 10 minutes to obtain only cells (pellet). The obtained cells were dispensed at $10^6$ cells/well in a 96-well plate, and each well was treated with 1 μg each of RSV-F and G protein at 2 μg/mL, and reacted at 37° C. for 5 hours. After washing the reacted cells with Facs staining buffer, the Fc blocker was diluted in staining buffer at a 1:1,000 ratio and treated with 100 μL/well, and the well plate was placed on ice and incubated for 15 minutes. The cells were treated with Ly6G, CD125, CD11b, and SiglecF antibodies at 1 μL/well, respectively, and the well plate was placed on ice and incubated for 30 minutes. The incubated cells were washed with Facs staining buffer, treated with 4% paraformaldehyde at 100 μL/well, and the well plate was placed on ice and incubated for 20 minutes. Thereafter, the cells were washed with Facs staining buffer, collected in 500 μL of staining buffer, and eosinophils were identified with a flow cytometer (C6 accuri, BD Bioscience), and the results are shown in FIG. 17A.

The mouse lung tissues obtained in Example 2-2 were subjected to H&E staining and prepared into slides. Three fields of view were randomly selected under a microscope at 400× magnification, and the number of eosinophils stained in pink was confirmed. Three mice were used for each group, and the eosinophils observed under the three fields of view randomly selected for each mouse were digitized, and the average data is shown in FIG. 17B.

Figure 17A:
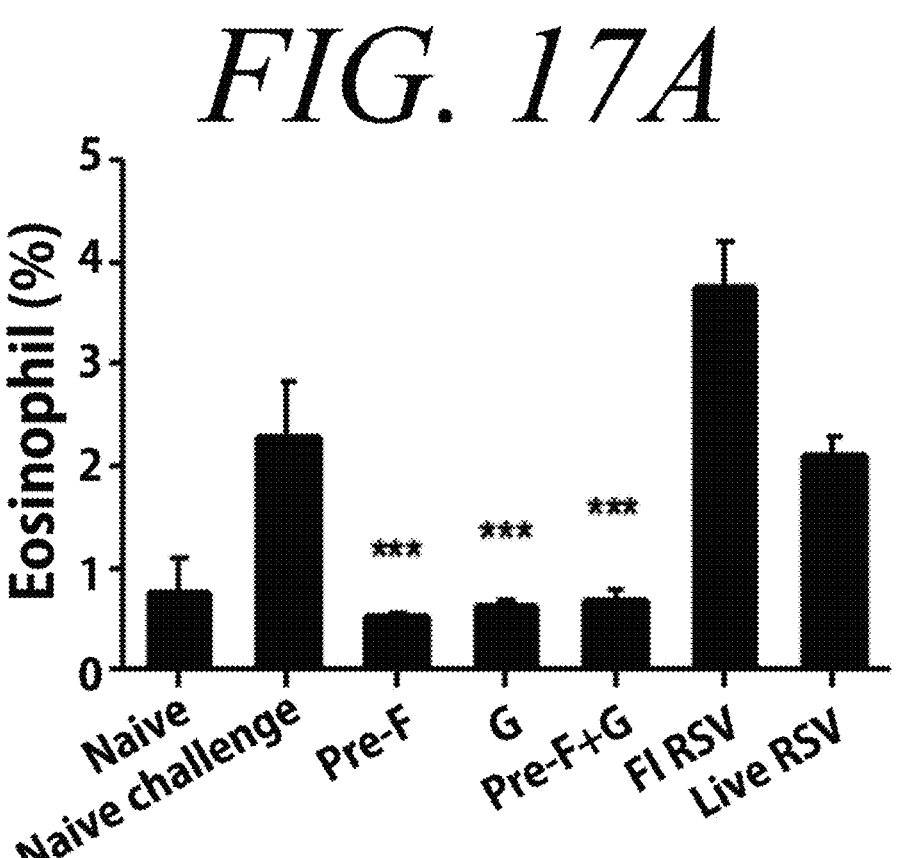
FIG. 17A shows the eosinophil count according to the vaccine treatment according to Example 2-1.
Figure 17B:
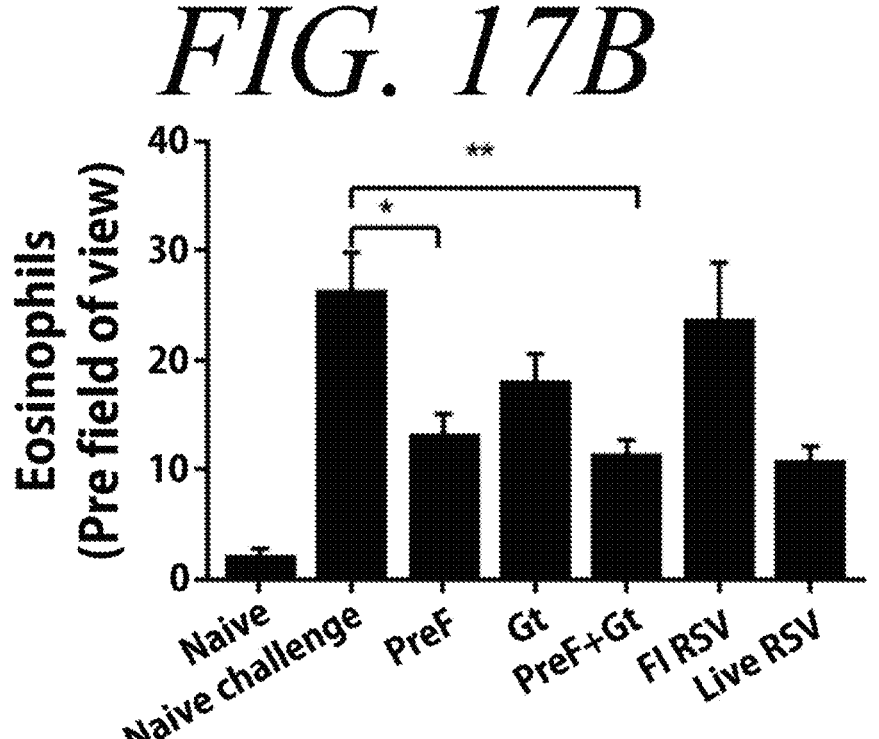
FIG. 17B shows the eosinophil count according to the vaccine treatment according to Example 2-2.

FIGS. 17A and 17B show eosinophil counts according to the vaccine treatment according to Example 2-1 and Example 2-2, respectively. According to FIGS. 17A and 17B, it was confirmed that all of the groups inoculated with RSV-preF, RSV-G, RSV-Gt, RSV-PreF+G, and RSV-PreF+Gt vaccines showed a lower increase in eosinophils compared to the unvaccinated infected group or the FI RSV-inoculated group thus not inducing a decrease in immunity due to vaccination.

What is claimed is:

1. A respiratory syncytial virus (RSV)-like particle comprising:

a core consisting of an influenza virus matrix protein 1 (M1); and an antigenic protein displayed on the surface of the core, wherein the antigen protein comprises a preF protein derived from RSV consisting of an amino acid sequence of SEQ ID NO: 12, and a chimeric protein, which comprises a first tandem sequence consisting of an amino acid sequence of SEQ ID NO: 9 and a second tandem sequence consisting of an amino acid sequence of SEQ ID NO: 10.

2. The RSV virus-like particle of claim 1, wherein the antigen protein further comprises:

an RSV-derived G protein consisting of an amino acid sequence of SEQ ID NO: 8.

3. The RSV virus-like particle of claim 2, wherein the chimeric protein is one in which the transmembrane domain and cytoplasmic tail domain of influenza hemagglutinin are linked to the C-terminus of the second tandem sequence.

4. The RSV virus-like particle of claim 2, wherein the chimeric protein is one in which the first tandem sequence and the second tandem sequence are linked by a linker.

5. A composition that induces an immune response against RSV infection comprising the RSV virus-like particle of claim 1 as an active ingredient.

6. The composition of claim 5, wherein the composition further comprises an adjuvant.

* * * * *